US012029555B2

(12) United States Patent
Rovatti et al.

(10) Patent No.: US 12,029,555 B2
(45) Date of Patent: Jul. 9, 2024

(54) SENSOR AND APPARATUS FOR DETERMINING AT LEAST ONE PARAMETER OF BLOOD CIRCULATING IN AN EXTRACORPOREAL BLOOD CIRCUIT

(71) Applicant: GAMBRO LUNDIA AB, Lund (SE)

(72) Inventors: Paolo Rovatti, Finale Emilia (IT); Enrico Ravagli, Bagnacavallo (IT); Stefano Severi, Rimini (IT)

(73) Assignee: GAMBRO LUNDIA AB, Lund (SE)

( * ) Notice: Subject to any disclaimer, the term of this patent is extended or adjusted under 35 U.S.C. 154(b) by 789 days.

(21) Appl. No.: 16/982,317

(22) PCT Filed: Mar. 20, 2019

(86) PCT No.: PCT/EP2019/056938
§ 371 (c)(1),
(2) Date: Sep. 18, 2020

(87) PCT Pub. No.: WO2019/180068
PCT Pub. Date: Sep. 26, 2019

(65) Prior Publication Data
US 2021/0015990 A1    Jan. 21, 2021

(30) Foreign Application Priority Data
Mar. 20, 2018   (EP) .................................... 18162977

(51) Int. Cl.
*A61B 5/145*      (2006.01)
*A61B 5/00*       (2006.01)
(Continued)

(52) U.S. Cl.
CPC ........ *A61B 5/14535* (2013.01); *A61B 5/0071* (2013.01); *A61B 5/0075* (2013.01);
(Continued)

(58) Field of Classification Search
CPC .............. A61M 1/1603; A61M 1/1605; A61M 1/1613; A61M 1/1619; A61M 1/3612;
(Continued)

(56) References Cited

U.S. PATENT DOCUMENTS

| 5,331,958 | A  | 7/1994 | Oppenheimer |
| 10,646,632 | B2 | 5/2020 | Rovatti et al. |

(Continued)

FOREIGN PATENT DOCUMENTS

| EP | 0693296 | 1/1996 |
| WO | 2016188950 | 1/2016 |

OTHER PUBLICATIONS

European Office Action Appln. No. 19 712 752.5-1113 dated Mar. 13, 2023—8 pages.
(Continued)

*Primary Examiner* — John Kim
(74) *Attorney, Agent, or Firm* — K&L Gates LLP

(57) ABSTRACT

An apparatus for extracorporeal treatment of blood (1) comprising a treatment unit (2), a blood withdrawal line (6), a blood return line (7), a preparation line (19) and a spent dialysate line (13); a non-invasive blood volume sensor (50) for determining an additional property of blood is active on a tube segment (61) of the blood withdrawal line or of the blood return line; the sensor includes one source (53) for directing a signal towards the blood, a plurality of detectors (57) for receiving the signal, and a controller (65) receiving the output signals from the detectors (57) and determining a blood volume variation and a value of sodium concentration in the blood ($Na_{pl}$) both based on the output signals. A process of determining at least one parameter and on property of blood circulating an extracorporeal blood circuit is also disclosed.

30 Claims, 10 Drawing Sheets

(51) Int. Cl.
 *A61B 5/02* (2006.01)
 *A61B 5/026* (2006.01)
 *A61B 5/1455* (2006.01)
 *A61B 8/00* (2006.01)
 *A61M 1/16* (2006.01)
 *A61M 1/36* (2006.01)

(52) U.S. Cl.
 CPC .......... *A61B 5/0261* (2013.01); *A61B 5/1455* (2013.01); *A61B 5/6866* (2013.01); *A61B 8/00* (2013.01); *A61M 1/1603* (2014.02); *A61M 1/1619* (2014.02); *A61M 1/3601* (2014.02); *A61M 1/3609* (2014.02); *A61M 1/3612* (2014.02); *A61M 1/3669* (2013.01); *A61B 2562/00* (2013.01); *A61B 2562/04* (2013.01); *A61B 2562/146* (2013.01); *A61B 2562/16* (2013.01); *A61B 2562/164* (2013.01); *A61B 2562/166* (2013.01); *A61B 2562/228* (2013.01); *A61M 1/1605* (2014.02); *A61M 1/1613* (2014.02); *A61M 2205/3306* (2013.01); *A61M 2205/3334* (2013.01)

(58) Field of Classification Search
 CPC .............. A61M 1/3601; A61M 1/3609; A61M 1/3669; A61M 2205/3306; A61M 2205/3334; A61B 5/0071; A61B 5/0075; A61B 5/0261; A61B 5/14535; A61B 5/1455; A61B 5/6866; A61B 8/00; A61B 2562/00; A61B 2562/04; A61B 2562/146; A61B 2562/16; A61B 2562/164; A61B 2562/166; A61B 2562/228
 See application file for complete search history.

(56) References Cited

U.S. PATENT DOCUMENTS

| | | |
|---|---|---|
| 2003/0023170 A1 | 1/2003 | Gardner et al. |
| 2011/0196215 A1 | 8/2011 | Ozawa |
| 2011/0269167 A1 | 11/2011 | Bene |
| 2015/0305658 A1 | 10/2015 | Islam |
| 2015/0343129 A1* | 12/2015 | Surace ................ A61M 1/1603 604/6.09 |
| 2016/0038666 A1 | 2/2016 | Kelly et al. |
| 2017/0013563 A1 | 5/2017 | Connor |
| 2017/0135633 A1 | 5/2017 | Connor |
| 2018/0169315 A1* | 6/2018 | Rovatti ............... A61M 1/1609 |

OTHER PUBLICATIONS

International Search Report; International Application No. PCT/EP2019/056938 dated Aug. 5, 2019;—6 Pages.

Written Opinion of the International Searching Authority; International Application No. PCT/EP2019/056938 dated Aug. 5, 2019—10 Pages.

Goureau Y et al, "Evaluation of Plasma Sodium Concentration During Hemodialysis by Computerization of Dialysate Conductivity", Asaio Transactions, Harper and Row Publishers, Hagerstown, MD, US, vol. 36, No. 3, Jul. 1, 1990 (Jul. 1, 1990), p. 444-447, XP000204537, p. M444.

Extended European Search Report; European Application No. 18162977.5; dated Sep. 17, 2018—11 Pages.

EP Office Action 19 712 752.5 1113 dated Nov. 14, 2023—9 pages.

* cited by examiner

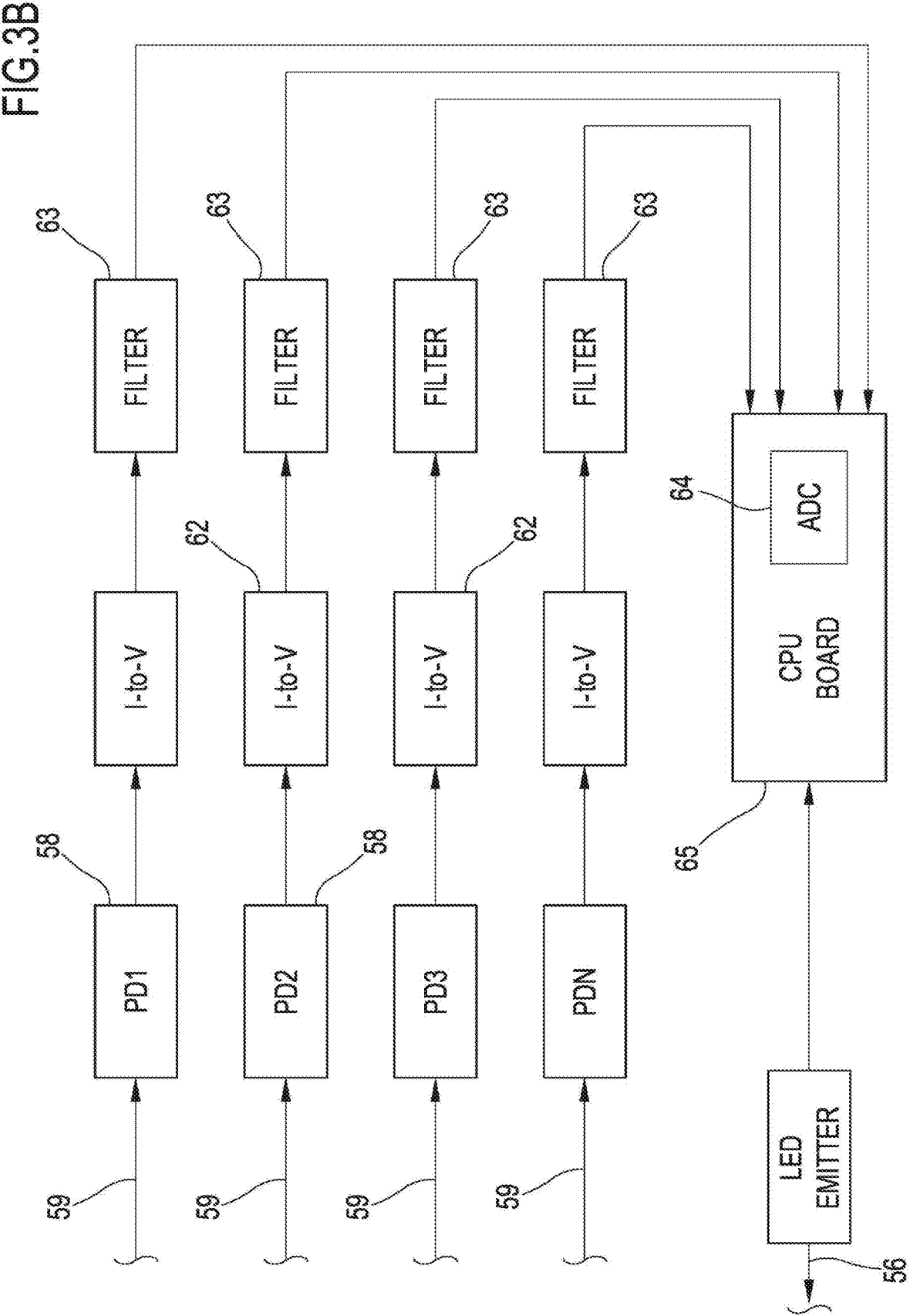

FIG.7
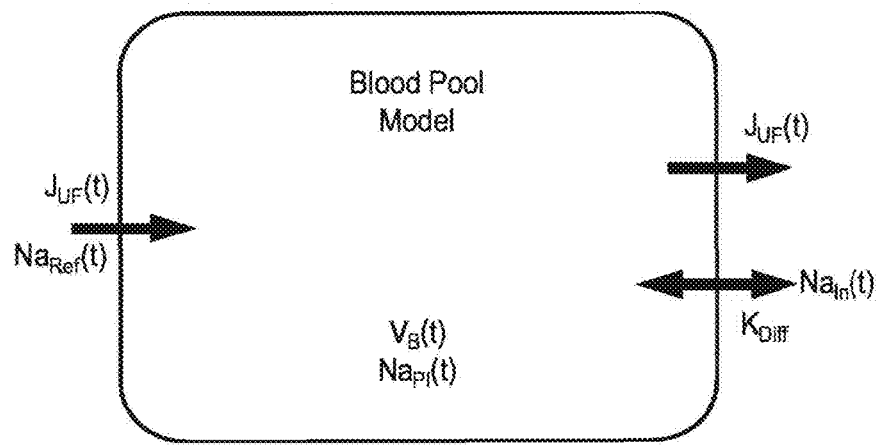
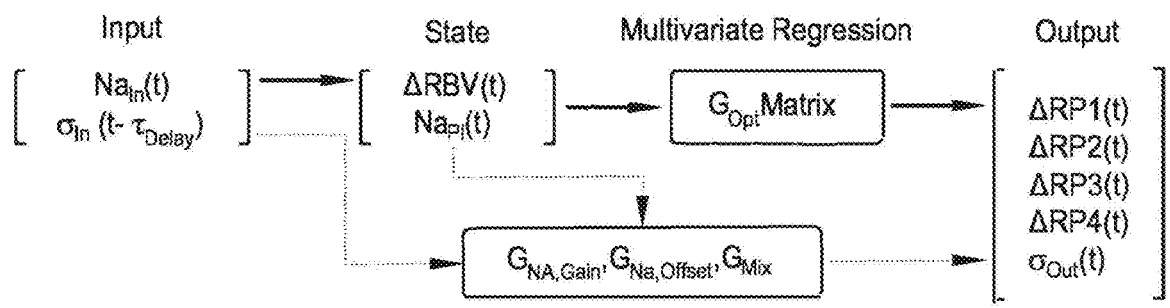
FIG.8
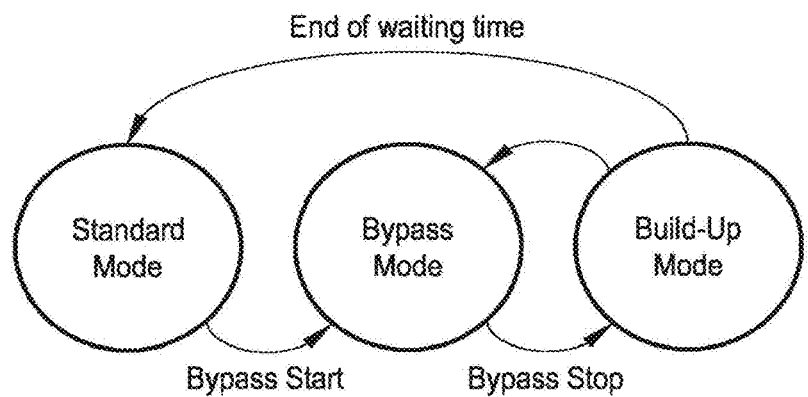
FIG.9

SENSOR AND APPARATUS FOR DETERMINING AT LEAST ONE PARAMETER OF BLOOD CIRCULATING IN AN EXTRACORPOREAL BLOOD CIRCUIT

PRIORITY CLAIM

The present application is a National Phase of International Application No. PCT/EP2019/056938, filed Mar. 20, 2019, which claims priority to EP Application No. 18162977.5, filed Mar. 20, 2018. The entire contents of each are incorporated herein by reference and relied upon.

DESCRIPTION

The invention relates to an apparatus, to a sensor and to a process for determining at least one parameter of blood circulating in an extracorporeal blood circuit. In particular, the apparatus, the sensor and process of the invention may serve for the non-invasive measure of the relative blood volume variation ($\Delta RBV$) and in more detail the percentage relative blood volume variation ($\Delta RBV$ %) and/or the blood or plasma sodium concentration ($Na_{pl}$) and/or the conductivity of plasma or blood circulating in an extracorporeal circuit. More in detail, the invention is directed the on-line measure of a blood parameter during an extracorporeal blood treatment or during extracorporeal plasma processing (e.g., hemodialysis, hemofiltration, hemodiafiltration, plasmapheresis etc.). The invention also relates to an apparatus and to a method for determining—based on the measure of the parameter of blood or plasma—a parameter indicative of the progress of an extracorporeal blood treatment, in particular a purification treatment, whose purpose is to alleviate renal insufficiency, such as hemodialysis or hemodiafiltration.

Although the apparatus, sensor and process of the invention may be applied to any extracorporeal blood or plasma processing, by way of example we will herein mainly refer to treatments such as hemodialysis or hemofiltration or hemodiafiltration.

Hemodialysis is a therapy employed for treating patients with chronic kidney injury, usually performed 3-4 times a week and lasting 3-5 hours. The treatment has three main goals of which the first is to remove excess body water accumulated between sessions, achieved by ultrafiltration (UF). The second goal is to remove uremic toxins, also accumulated between sessions. The third goal is to restore the proper balance of electrolytes in the blood.

In an hemodialysis treatment a patient's blood and a treatment liquid approximately isotonic with blood flow are circulated in a respective compartment of hemodialyzer, so that, impurities and undesired substances present in the blood (urea, creatinine, etc.) may migrate by diffusive transfer from the blood into the treatment liquid. The ion concentration of the treatment liquid is chosen such as to correct the ion concentration of the patient's blood. In other terms, hemodialysis is based on the two phenomena of diffusion and convection, with which mass transfer of water and solutes across the membrane of the hemodialysis filter (hemodialyzer) is achieved. The hemodialyzer is a cylindrical bundle of hollow fibers designed to maximize the exchange surface area. Inside, blood and dialysis fluid (dialysate) flow in counter-current on opposite sides of the membrane.

In hemofiltration, a convective transfer by ultrafiltration takes place across the semipermeable membrane of a hemofilter. In a treatment by hemodiafiltration, a convective transfer by ultrafiltration, resulting from a positive pressure difference created between the blood side and the treatment-liquid side of the semi-permeable membrane, is added to the diffusive transfer obtained by dialysis.

In these type of treatments, it is of interest to be able to determine one or more parameters indicative of how the treatment is impacting or has impacted on the treated blood. Online monitoring of certain blood parameters may, on the other hand, allow to modify treatment conditions that were initially fixed or to at least inform the patient and the medical personnel about how the treatment is progressing. The knowledge of one or more of the following parameters:

the concentration of one or more electrolytes in the extracorporeal blood or plasma, the conductivity of the extracorporeal blood or plasma, the blood volume variation, e.g. the relative blood volume loss, during a treatment session, the actual dialysance D or the actual clearance K of the exchanger for a given solute (the dialysance D and the clearance K representing the purification efficiency of the exchanger), the dialysis dose administered after a treatment time t, which, according to the work of Sargent and Gotch, may be linked to the dimensionless ratio Kt/V, where K is the actual clearance in the case of urea, t the elapsed treatment time and V the volume of distribution of urea, i.e. the total volume of water in the patient (Gotch F. A. and Sargent S. A., "A mechanistic analysis of the National Cooperative Dialysis Study (NCDS)", Kidney Int. 1985, Vol. 28, pp. 526-34), may allow to follow progress of the treatment, and thus may help to assess the suitability of initially fixed treatment conditions or to establish whether the treatment unit is adequately performing or to assess presence of access recirculation.

The determination of the above parameters requires precise knowledge of a physical or chemical characteristic of the blood or plasma. As it can be understood, determination of this characteristic could—in principle—be obtained by direct measurement on a specimen of blood. However, for therapeutic, prophylactic and financial reasons, it is out of the question taking multiple specimens necessary to monitor the effectiveness of the treatment from a patient who is often anemic; furthermore, given the risks associated with handling specimens of blood which may possibly be contaminated, the general tendency is to avoid such handling operations; finally, laboratory analysis of a specimen of blood is both expensive and relatively lengthy, this being incompatible with a desirable objective of knowing the effectiveness of a treatment while the treatment is still ongoing.

In modern hemodialysis, much emphasis has been placed on the development of non-invasive methods for the collection of physiological information, carried out either by applying sensors directly on the patient or by accessing the hemodialysis machine during the treatment. In addition to being important for patient safety and to gather clinical knowledge, continuous or semi-continuous monitoring of physiological parameters is especially important as input to biofeedback systems.

Examples of physiological parameters subject to investigation are relative blood volume variation ($\Delta RBV$ %), dialysance (D) and plasmatic electrical conductivity ($\sigma_{Pl}$). Blood volume variation ($\Delta RBV$) quantifies the effect of UF, and is today continuously monitored by optical or ultrasonic means. The parameter D quantifies dialysis efficiency, and can change during treatment. $\sigma_{Pl}$ is a surrogate for plasmatic sodium concentration $Na_{Pl}$, which currently cannot be measured in a direct, continuous and non-invasive way.

Several known methods have been proposed for in vivo determining blood concentration, or other hemodialysis parameters such as blood volume variation and plasma conductivity, without having to take measurements on blood samples.

For instance, using a urea sensor in the spent dialysate line, it is possible to calculate urea concentration in blood. Urea sensors are however complex, expensive and may not lead to accurate measures. In accordance with a second approach, blood conductivity or blood electrolyte concentration may be measured by imposing periodic changes in the concentration of a given substance or in the conductivity of the dialysis liquid at the inlet of the blood treatment unit (filter or hemodialyzer) and by measuring the corresponding effect in term of concentration for the same substance or conductivity change in the spent dialysate. The following patent references disclose methods for the in vivo determination of blood conductivity, blood concentration for a given substance, dialysance and other parameters perturbing the fresh dialysis liquid and taking measures of concentration/conductivity on the dialysate side of the apparatus: EP 0547025, EP 0658352, EP 0920877, US 2001004523, EP 2687248, U.S. Pat. Nos. 6,187,199, 5,100,554. The problem with this second type of approach is that there is a need to perturb the composition of the fresh dialysis liquid, in order to then determine—with more or less complex calculations—the sought parameter, e.g., sodium concentration in blood and/or sodium dialysance. Furthermore, concentration/conductivity in the liquid downstream the dialyzer may be difficult to be measured with high accuracy. Moreover, the hydraulic delay, the damping effect caused by the dialyzer, and the noise introduced by the machine and its components may require to appropriately elaborate the signals detected by the sensors. Additionally, all above methods, require calculations which may be relatively complex to then arrive at the determination of blood sodium concentration or blood conductivity.

Finally, U.S. Pat. No. 8,525,533 uses a conductivity sensor applied to the spent dialysate line and capable of determining conductivity of the used dialysis liquid. In accordance with this reference, the conductivity sensor requires four electrodes, namely two ring-shaped excitation electrodes and two ring shaped pick-up electrodes. As the sensor is applied to the dialysate line, in order to determine a blood parameter it would be necessary to adopt one of the methods disclosed above with the drawbacks that have been just described.

Referring now to relative blood volume variation ($\Delta$RBV), online measurement of this specific blood parameter generally uses an optical approach. Optical $\Delta$RBV estimation is based on the absorbance of hemoglobin (Hgb), which is almost completely contained inside the red blood cells. In simple optical sensors, a LED and a photodiode are used to detect absorbance changes linked to variations in red blood cell concentration. The number of red blood cells is nearly constant during treatment, so hemoconcentration is mainly caused by a water removal due to UF that is larger than the plasma refilling rate.

Known sensor works measuring only light transmitted through blood at 180° from the illuminating infrared LED. This measurement, absorbance, is dependent on hematocrit changes, so it is used for an estimation of relative blood volume loss.

Other devices for measuring relative blood volume loss makes use of a reflectance sensor to measure light reflected by blood. In this case the illuminating LED and the optical sensor are placed on the same side of the cuvette, at a certain distance.

Ultrasound sensors are also used to measure RBV loss as a function of total protein concentration.

Moreover, an optical system with multiple LEDs for measurements at different wavelengths is also used for estimation of oxygen saturation and for calibration purposes.

The use of optical sensors for blood applications is diffused, but most implementation use just one measurement channel. When multiple channels are used, it is mostly to detect light at different wavelengths for purposes like estimation of oxygen saturation or additional calibration (for example, to compensate for the effect of temperature).

Recently, it was reported that $\Delta$RBV estimation by optical sensors is afflicted by a cross-sensitivity to changes in concentration of electrolytes. Drastic changes in dialysate sodium concentration can lead to under- or overestimation of $\Delta$RBV. Such changes can be explained by considering the action of osmolarity on red blood cell volume. Sodium, being one of the highest-concentrated solutes in both dialysate and plasma, is a main driver of osmolarity. Dialysate sodium variations propagate to plasma due to diffusion across the hemodialyzer membrane. Consequently, a water shift takes place across the membrane of red blood cells to balance inner and outer osmolarity, thereby changing their volume. This volume variation alters local Hgb concentration and leads to a modification of the absorbance and scattering properties of blood. Although the relationship between hemoconcentration, osmolarity and the optical properties of blood is subject to investigation, the influence of osmolarity on $\Delta$RBV estimation is still an important issue to deal with because in certain treatments the physician may set a blood volume variation target to be reached at the end of the treatment and the $\Delta$RBV estimate can be used as feedback to control the UF in order to reach the target. Moreover, in order to improve the patient well-being, huge blood volume variations have to be avoided, or, in different terms, the blood volume variation is to be profiled during the course of the treatment session. Clearly, an inaccurate $\Delta$RBV estimation may lead to an incorrect trajectory for end-session water removal.

In whole blood, light propagation along different trajectories takes different names: transmittance, reflectance, scattering.

In an approach according to document WO0033053, the measuring system is a modification of the device measuring only light transmitted through blood at 180° from the illuminating infrared LED by adding a sensor with a 90° additional channel. The additional channel has mainly calibrations and/or correction purposes. The prior art computing unit is arranged to calculate a ratio signal by dividing the scattered light signal provided by a scattered light diode and the transmitted light signal provided by a transmitted light diode to provide an optical ratio signal. According to document WO0033053, it has been found that the ratio between the perpendicular scattered signal and the transmitted signal is essentially proportional to the red cell concentration, i.e. there is a linear relationship between the ratio signal and the red cell concentration. The ratio signal has, moreover, merely a small dependency on oxygen saturation level, osmolarity and blood flow rate.

It is also known from document U.S. Pat. No. 5,331,958A1 a method and device which are useful for continuous on-line monitoring of hematocrit and other blood parameters. According to this prior art, the effect of change in blood electrolyte composition, for example, in blood sodium concentration, is taken into consideration. This effect has been found to change light beam geometry, and is taken advantage of to provide for blood sodium concentration measurement. The devices may be applied to extracorporeal circuits or to body parts capable of being transilluminated. The devices may be used to optimize dialysis, and also for monitoring optically detectable, exogenous macromolecules.

In the present situation it is an object of the present invention to provide an apparatus, a sensor and a process able to reliably determine at least one parameter, such as the blood volume variation ($\Delta$RBV) and/or the blood or plasma sodium concentration ($Na_{pl}$) and/or the plasma or blood conductivity ($\sigma_{pl}$), of blood or plasma circulating in the extracorporeal blood circuit.

It is also an object of embodiments of the invention to offer an apparatus and process which do not require blood or plasma sampling for the determination of the parameter of interest and which can operate continuously and effectively during the execution of an extracorporeal blood or plasma treatment or processing.

Another aim is to develop an apparatus and a method for accurate estimation of blood concentration and osmolarity during, e.g. a hemodialysis treatment, particularly represented by $\Delta$RBV and Napa, which are considered to be a simple, yet highly descriptive set of physiological parameters.

It is also an object of embodiments of the invention to allow proper determination of one or more blood parameters without impairing on the treatment prescription and, particularly, with no need to introduce perturbations in either the dialysate circuit or the blood circuit.

Additionally, it is an object providing a process and an apparatus which may be implemented with no need of high computational power and without complex mathematical models.

Another auxiliary object is an apparatus capable of operating in a safe manner.

A further auxiliary object is an apparatus and process allowing—based on the determination of the one or more blood or plasma parameters—calculate a parameter indicative of the effectiveness of the treatment, such as dialysance and/or dialysis dose.

SUMMARY

At least one of the above objects is substantially reached by an apparatus and/or by a sensor and/or by a process according to one or more of the appended claims.

Apparatus and processes according to aspects of the invention and capable of achieving one or more of the above objects are here below described.

A $1^{st}$ aspect concerns a non-invasive sensor (50), in particular a blood volume sensor, for determining at least one property and/or one (auxiliary) parameter of blood flowing in an extracorporeal segment (61), e.g. a tube segment, of an extracorporeal blood treatment apparatus comprising:
- at least one source (53) for directing a signal towards the blood along an emission axis (54);
- a plurality of detectors (57) for receiving the signal emitted by said source (53) after at least partially passing through the blood flowing in the segment (61) and emitting respective output signals related to the received signal,
- a controller (65) configured for receiving the respective output signals from the plurality of detectors (57) and for determining a value of said property of blood and/or parameter based on the output signals, in particular wherein said property of blood is blood volume variation or hemoglobin concentration or a parameter directly related to blood volume variation or hemoglobin concentration.

In the following aspects, the extracorporeal segment (61) is referred to as a tube segment, in a non-limiting way. Each time tube segment is mentioned it is intended that also extracorporeal segment is alternatively mentioned and may be substituted to the more limiting term.

In $2^{nd}$ aspect according to the $1^{st}$ aspect, the controller (65) is further configured to determine a value of an (auxiliary) blood parameter, said auxiliary parameter being chosen in the group including plasma conductivity ($\sigma_{pl}$), a plasma conductivity-related parameter, concentration of at least one substance in the blood ($Na_{pl}$), e.g. sodium, and a concentration-related parameter of at least one substance in the blood.

In a $3^{rd}$ aspect according to anyone of the previous aspects, the controller (65) is further configured to determine a value of the property of blood based on the output signals from the plurality of detectors (57).

In a $4^{th}$ aspect according to anyone of the previous aspects, the controller (65) is configured to determine a time variation of said auxiliary blood parameter based on the output signals.

In a $5^{th}$ aspect according to any one of the preceding aspects, the controller (65) is configured to determine a time variation of said property of blood based on the output signals.

In a $6^{th}$ aspect according to any one of the preceding aspects, the controller (65) is configured to receive values for a sodium concentration ($Na_{in}$) of an inlet dialysis fluid flowing in a preparation line (19) of the extracorporeal blood treatment apparatus (1), the controller (65) being configured to determine the value of said auxiliary blood parameter based on the inlet dialysis fluid sodium concentration ($Na_{in}$).

In a $7^{th}$ aspect according to any one of the preceding aspects, the controller (65) is configured to receive values for a sodium concentration ($Na_{in}$) of an inlet dialysis fluid flowing in a preparation line (19) of the extracorporeal blood treatment apparatus (1), the controller (65) being configured to determine the value of said property of blood based on the inlet dialysis fluid sodium concentration ($Na_{in}$).

In an $8^{th}$ aspect according to any one of the preceding aspects, the controller (65) is configured to receive values for a conductivity ($\sigma_{in}$) of an inlet dialysis fluid flowing in a preparation line (19) of the extracorporeal blood treatment apparatus (1), the controller (65) being configured to determine the value of said auxiliary blood parameter based on the inlet dialysis fluid conductivity ($\sigma_{in}$).

In a $9^{th}$ aspect according to any one of the preceding aspects, the controller (65) is configured to receive values for a conductivity ($\sigma_{in}$) of an inlet dialysis fluid flowing in a preparation line (19) of the extracorporeal blood treatment apparatus (1), the controller (65) being configured to determine the value of said property of blood based on the inlet dialysis fluid conductivity ($\sigma_{in}$).

In a $10^{th}$ aspect according to the preceding two aspects, the controller (65) is configured to receive measured values for the inlet dialysis fluid conductivity ($\sigma_{in}$).

In an $11^{th}$ aspect according to the preceding aspects 8 or 9, the controller (65) is configured to receive set values for the inlet dialysis fluid conductivity ($\sigma_{in}$).

In a 12$^{th}$ aspect according to the preceding aspects 6 or 7, the controller (65) is configured to receive measured values for the inlet dialysis fluid sodium concentration ($Na_{in}$).

In a 13$^{th}$ aspect according to the preceding aspects 6 or 7, the controller (65) is configured to receive set values for the inlet dialysis fluid sodium concentration ($Na_{in}$).

In a 14$^{th}$ aspect according to any one of the preceding aspects, the controller (65) is configured to receive values for a conductivity ($\sigma_{out}$) of an outlet dialysis fluid flowing in a spent dialysate line (13) of the extracorporeal blood treatment apparatus (1), the controller (65) being configured to determine the value of said auxiliary blood parameter based on the outlet dialysis fluid conductivity ($\sigma_{out}$).

In a 15$^{th}$ aspect according to any one of the preceding aspects, the controller (65) is configured to receive values for a conductivity ($\sigma_{out}$) of an outlet dialysis fluid flowing in a spent dialysate line (13) of the extracorporeal blood treatment apparatus (1), the controller (65) being configured to determine the value of said property of blood based on the outlet dialysis fluid conductivity ($\sigma_{out}$).

In a 16$^{th}$ aspect according to the preceding aspects 14 or 15, the controller (65) is configured to receive measured values for the outlet dialysis fluid conductivity ($\sigma_{out}$).

In a 17$^{th}$ aspect according to any one of the preceding aspects, the controller (65) is configured for using a state-space mathematical modeling for determining said property of blood and/or said auxiliary blood parameter, wherein the state-space mathematical modeling includes the following equations:

$$\Delta \dot{R}BV(t) = 0 \quad (6)$$

$$N\dot{a}_{Pl}(t) = \frac{Na_{In}(t) - Na_{Pl}(t)}{\tau_{Diff}} \quad (7)$$

wherein

| | |
|---|---|
| $\Delta \dot{R}BV$ (t) | Differential relative blood volume |
| $N\dot{a}_{Pl}$ (t) | Differential plasma sodium concentration in tube segment 61 at instant t |
| $Na_{Pl}$ (t) | Plasma sodium concentration in tube segment 61 at instant t |
| $Na_{In}$ (t) | Inlet dialysate sodium concentration at instant t at the inlet of the filtration unit |
| $\tau_{Diff}$ | Diffusion time |

In a 18$^{th}$ aspect according to the preceding aspect, the diffusion time ($\tau_{Diff}$) is equal to:

$$\tau_{Diff} = \frac{V_B(t)}{K_{Diff}}$$

wherein

| | |
|---|---|
| $V_B$ (t) | Absolute blood volume at instant t |
| $K_{Diff}$ | Semipermeable membrane diffusion coefficient for sodium |

In a 19$^{th}$ aspect according to any one of the preceding two aspects, the diffusion time ($\tau_{Diff}$) is approximate to a constant time, included between, e.g. 1000 and 1200 s.

In a 20$^{th}$ aspect according to any one of the preceding aspects, the controller (65) is configured to determine both said property of blood and an auxiliary blood parameter based on the output signals from the plurality of detectors (57) using a mathematical equation linearly combining values of the property of blood, of the auxiliary blood parameter and of the output signals.

In a 21$^{st}$ aspect according to any one of the preceding aspects, the controller (65) is configured to determine both said property of blood and an auxiliary blood parameter based on the output signals from the plurality of detectors (57) using the following mathematical equation:

$$\Delta RP_i(t) = G_{Opt,i,1} \cdot \Delta RBV(t) + G_{Opt,i,2} \cdot Na_{Pl} + G_{Opt,i,3} \quad (8)$$

wherein

| | |
|---|---|
| $\Delta RP_i$ (t) | Optical output of detector i |
| $G_{Opt, i, 1}$ | Coefficients 1 to 3 for the output signal from i-detector |
| $G_{Opt, i, 2}$ | |
| $G_{Opt, i, 3}$ | |
| $\Delta RBV$ (t) | Relative blood volume |
| $Na_{Pl}$ (t) | Plasma sodium concentration in tube segment 61 at instant t |

In a 22$^{nd}$ aspect according to any one of the preceding aspects, the controller (65) is configured for using a state-space mathematical modeling for determining said property of blood and/or said auxiliary blood parameter, wherein in a by-pass condition of the extracorporeal blood treatment apparatus where the inlet dialysis fluid is not routed into, and by-passes, a filtration unit, the state-space mathematical modeling includes the following equations:

$$\Delta \dot{R}BV(t) = 0 \quad (6)$$

$$N\dot{a}_{Pl}(t) = 0 \quad (13)$$

wherein

| | |
|---|---|
| $\Delta \dot{R}BV$ (t) | Differential relative blood volume |
| $N\dot{a}_{Pl}$ (t) | Differential plasma sodium concentration in tube segment 61 at instant t |

In a 23$^{rd}$ aspect according to any one of the preceding aspects, the controller (65) is configured for determining the auxiliary blood parameter also based on an outlet dialysis fluid conductivity ($\sigma_{out}$) modeled as an average, in particular a weighted average, of an inlet dialysis fluid conductivity ($\sigma_{in}$) and of a plasma conductivity ($\sigma_{pl}$), wherein the outlet dialysis fluid conductivity ($\sigma_{out}$) is the conductivity of a dialysis fluid flowing in a spent dialysate line (13) of the extracorporeal blood treatment apparatus, the inlet dialysis fluid conductivity ($\sigma_{in}$) is the conductivity of a dialysis fluid flowing in a preparation line (19) of the extracorporeal blood treatment apparatus and the plasma conductivity ($\sigma_{pl}$) being the conductivity of the blood flowing in the tube segment (61).

In a 24$^{th}$ aspect according to any one of the preceding aspects, the controller (65) is configured for determining the auxiliary blood parameter also based on the following mathematical relationship:

$$\sigma_{Out}(t) = G_{Mix} \cdot \sigma_{Pl}(t) + (1 - G_{Mix}) \cdot \sigma_{in}(t - \tau_{Delay}) \quad (11)$$

wherein

| | |
|---|---|
| $\sigma_{in}$(t) | Inlet dialysate conductivity at instant t at the inlet of the filtration unit |

-continued

| | |
|---|---|
| $\sigma_{Out}(t)$ | Outlet dialysate conductivity at instant t at the outlet of the filtration unit |
| $\sigma_{pl}(t)$ | Plasmatic conductivity in tube segment 61 at instant t |
| $G_{Mix}$ | Weighing coefficient, e.g. equal to $\frac{D}{J_D}$ |
| $\tau_{Delay}$ | Delay time to account for the propagation time of changes in the inlet dialysate composition across the hydraulic circuit |

In a 25$^{th}$ aspect according to the preceding aspect, the weighing coefficient ($G_{Mix}$) is proportional, and in particular equal, to:

$$G_{Mix} = \frac{D}{J_D}$$

wherein

| | |
|---|---|
| D | Treatment unit dialysance |
| $J_D$ | Dialysis flow rate |

In a 26$^{th}$ aspect according to any one of the preceding two aspects, the weighing coefficient ($G_{Mix}$) is a constant, e.g. included between 0.4 and 0.6.

In a 27$^{th}$ aspect according to any one of the preceding three aspects, the delay time ($\tau_{Delay}$) to account for the propagation time of changes in the inlet dialysate composition across the hydraulic circuit is a constant, e.g. included between 100 s and 200 s.

In a 28$^{th}$ aspect according to any one of the preceding aspects, the controller (65) is configured for determining the auxiliary blood parameter also based on a plasma conductivity ($\sigma_{pl}$), being the conductivity of the blood flowing in the tube segment (61).

In a 29$^{th}$ aspect according to any one of the preceding aspects, the controller (65) is configured for determining the auxiliary blood parameter also based on the following mathematical relationship:

$$\sigma_{Pl}(t) = G_{Na,Gain} \cdot Na_{Pl}(t) + G_{Na,Offset} \quad (12)$$

wherein

| | |
|---|---|
| $\sigma_{pl}(t)$ | Plasmatic conductivity in tube segment 61 at instant t |
| $G_{Na, Gain}$ | Constant coefficient |
| $G_{Na, Offset}$ | Constant coefficient |
| $Na_{Pl}(t)$ | Plasma sodium concentration in tube segment 61 at instant t |

In a 30$^{th}$ aspect according to any one of the preceding aspects, the controller (65) is configured for using a Kalman filter for determining said property of blood and/or said auxiliary blood parameter.

In a 31$^{st}$ aspect according to anyone of the preceding aspects, the controller (65) is configured for using a Kalman filter for determining said property of blood and/or said auxiliary blood parameter, the Kalman filter including a prediction step based on the following equations:

$$x_k^- = f(x_{k-1}^+, u_k) \quad (14)$$

$$P_k^- = A \cdot P_{k-1}^+ \cdot A^T + Q \quad (15)$$

wherein
equations (14) and (15) are given as a function of the generic time step k, e.g. 1 s;
$u_k$ being a [2×1] vector which includes inlet dialysate sodium concentration at time step k at the inlet of the filtration unit ($Na_{In}[k]$) and inlet dialysis fluid conductivity at time step k ($\sigma_{In}[k]$) $x_k^-$ and $x_k^+$ being [2×1] vectors containing respectively predicted and corrected values of the auxiliary blood parameter, in particular plasma sodium concentration ($Na_{Pl}[k]$), and the property of blood, namely relative blood volume variation at time step k ($\Delta RBV[k]$), plasma sodium concentration and relative blood volume variation being the state variables; $x_k^-$ being the predicted system state at step k, and being a function of $x_{k-1}^+$ and $u_k$;
Q being a [2×2] matrix describing process noise covariance. A being a [2×2] Jacobian matrix linearization of function f(•,•) with respect to relative blood volume variation ($\Delta RBV$) and plasma sodium concentration ($Na_{p1}$).
$P_k^-$ and $P_k^+$ are the predicted and corrected [2×2] estimation covariance matrices, respectively computed at each step k, according to equations (15) and (18).

In a 32$^{nd}$ aspect according to the preceding aspect, the initial vector $x_0^+$ is set to a null blood volume variation, namely $\Delta RBV=0$, and plasma sodium concentration equal to a subject average plasma sodium concentration, such as $Na_{p1}=140$ mM.

In a 33$^{rd}$ aspect according to any one of the preceding two aspects, the initial diagonal matrix $P^+$ is set to a null blood volume variation, namely $\Delta RBV=0$, and plasma sodium concentration ($Na_{pl}$) equal to a value less than 6 mM, preferably equal to 4 mM.

In a 34$^{th}$ aspect according to any one of the preceding three aspects, function f(•,•) is defined by a discretized versions of equations according to aspect 17 in treatment mode.

In a 35$^{th}$ aspect according to the preceding four aspects, function f(•,•) is defined by a discretized versions of equations according to aspect 22 in by-pass mode.

In a 36$^{th}$ aspect according to any one of the preceding aspects, discretized versions of equations according to aspect 17 in treatment mode are as follows:

$$\Delta RBV[k] = \Delta RBV[k-1] \quad (19)$$

$$Na_{Pl}[k] = Na_{Pl}[k-1] \cdot \left(1 - \frac{1}{\tau_{Diff}}\right) + \frac{1}{\tau_{Diff}} \cdot Na_{In}[k]$$

wherein a forward Euler method for discretization is used.

In a 37$^{th}$ aspect according the any one of preceding aspects 31 to 35, the Kalman filter includes a measurement-based correction step based on the following equations:

$$E_k = P_k^- \cdot H^T \cdot (H \cdot P_k^- \cdot H^T + R)^{-1} \quad (16)$$

$$x_k^+ = x_k^- + E_k \cdot (z_k - g(x_k^-, u_k)) \quad (17)$$

$$P_k^+ = (I - E_k \cdot H) \cdot P_k^- \quad (18)$$

wherein
$E_k$ being a [2×5] error gain matrix computed according to equation (16);
R being a [5×5] covariance diagonal matrix, in particular the diagonal values of R, associated with optical measurements, are set equal to a root-mean-square fitting residuals of equation (9):

$$\begin{bmatrix} \Delta RP_1(t) \\ \Delta RP_2(t) \\ \Delta RP_3(t) \\ \Delta RP_4(t) \end{bmatrix} = G_{Opt} \cdot \begin{bmatrix} \Delta RBV(t) \\ Na_{Pl}(t) \\ 1 \end{bmatrix} \quad (9)$$

wherein

| | |
|---|---|
| $\Delta RP_i(t)$ | Optical output of detector i |
| $G_{Opt}$ | [4 × 3] matrix including weighting coefficients for the output signal from detectors |
| $\Delta RBV(t)$ | Relative blood volume |
| $Na_{Pl}(t)$ | Plasma sodium concentration in tube segment 61 at instant t | the diagonal value of R associated with outlet dialysis conductivity ($\sigma_{out}$) is a deviation of dialysance (D) from an average value of e.g. 250 ml/min;
$Z_k$ is a [5×1] observation column vector of measured output, composed of the signal outputs ($\Delta RP_1[k]$ to $\Delta RP_4[k]$) and outlet conductivity ($\sigma_{Out}[k]$);
$g(x_k^-, u_k)$ is a [5×1] column vector of predicted output calculated according to state-output function $g(\cdot,\cdot)$. The function $g(\cdot,\cdot)$ is determined by time-discrete equations (22), (23) and (24), given by:

$$\begin{bmatrix} \Delta RP_1(k) \\ \Delta RP_2(k) \\ \Delta RP_3(k) \\ \Delta RP_4(k) \end{bmatrix} = G_{Opt} \cdot \begin{bmatrix} \Delta RBV(k) \\ Na_{Pl}(k) \\ 1 \end{bmatrix} \quad (22)$$

$$\sigma_{Out}[k] = G_{Mix} \cdot \sigma_{Pl}[k] + (1 - G_{Mix}) \cdot \sigma_{In}[k - k_{Delay}] \quad (23)$$

$$\sigma_{Pl}[k] = G_{Na,Gain} \cdot Na_{Pl}[k] + G_{Na,Offset} \quad (24)$$

wherein

| | |
|---|---|
| $\Delta RP_i(k)$ | Optical output of detector i at time step k |
| $G_{Opt}$ | [4 × 3] matrix including weighting coefficients for the output signal from detectors |
| $\Delta RBV(k)$ | Relative blood volume at time step k |
| $Na_{Pl}(k)$ | Plasma sodium concentration in tube segment 61 at time step k |
| $\sigma_{in}(k)$ | Inlet dialysate conductivity at time step k at the inlet of the filtration unit |
| $\sigma_{Out}(k)$ | Outlet dialysate conductivity at time step k at the outlet of the filtration unit |
| $\sigma_{pl}(k)$ | Plasmatic conductivity in tube segment 61 at time step k |
| $G_{mix}$ | Weighing coefficient, e.g. equal to $\dfrac{D}{J_D}$ |
| $k_{Delay}$ | Delay time to account for the propagation time of changes in the inlet dialysate composition across the hydraulic circuit |
| $G_{Na,Gain}$ | Constant coefficient |
| $G_{Na,Offset}$ | Constant coefficient |
| $Na_{Pl}(k)$ | Plasma sodium concentration in tube segment 61 at time step k |

H is the [5×2] Jacobian linearization matrix of function $g(\cdot,\cdot)$ in respect to relative blood volume variation ($\Delta RBV$) and plasma sodium concentration ($Na_{p1}$).

In a 38th aspect a non-invasive sensor (50), in particular a blood volume sensor, is provided for determining at least one property of blood and/or one auxiliary blood parameter flowing in an extracorporeal segment (61), e.g. a tube segment, of an extracorporeal blood treatment apparatus comprising:

at least one source (53) for directing a signal towards the blood along an emission axis (54);
a plurality of detectors (57) for receiving the signal emitted by said source (53) after at least partially passing through the blood flowing in the segment (61) and emitting respective output signals related to the received signal.

In a 39th aspect according to any one of the preceding aspects, at least one detector, and in particular all detectors, includes a photodiode receiver.

In a 40th aspect according to any one of the preceding aspects, the source includes an electromagnetic radiation source or an ultrasound source.

In a 41st aspect according to any one of the preceding aspects, the source includes a light source, in particular a LED source.

In a 42nd aspect according to any one of the preceding aspects, the source includes a multiple wavelength LED emitter including multiple LEDs, e.g. 5 LEDs, on a same chip with pick wavelengths in the red and infrared bands.

In a 43rd aspect according to any one of the preceding aspects, an illuminating peak wavelength of the source is comprised between 790 and 820 nm, in particular between 800 and 810 nm.

In a 44th aspect according to any one of the preceding aspects, the source includes a fiber optic having one end coupled with the signal emitter and the other end placed to direct the emitted signal towards the blood along the emission axis.

In a 45th aspect according to any one of the preceding aspects, said detectors are placed at different angular degrees with respect to the emission axis.

In a 46th aspect according to any one of the preceding aspects, said detectors substantially contemporaneously receives the same signal emitted by the source after transmission and/or reflection and/or scattering through the blood flowing in the tube segment.

In a 47th aspect according to any one of the preceding aspects, said detectors collect reflected signal, scattered signal and/or transmitted signal depending on their respective position.

In a 48th aspect according to any one of the preceding aspects, said detectors collect reflected electromagnetic radiation, scattered electromagnetic radiation and/or transmitted electromagnetic radiation depending on their respective position.

In a 49th aspect according to any one of the preceding aspects, at least one detector is placed at about 180° with respect to the emission axis of the source and/or at least another detector is placed at about 45° with respect to the emission axis of the source.

In a 50th aspect according to any one of the preceding aspects, at least one detector is placed at about 90° with respect to the emission axis of the source and/or at least another detector is placed at about 0° with respect to the emission axis of the source.

In a 51st aspect according to any one of the preceding aspects, the sensor includes four different detectors for receiving the electromagnetic radiation from the source, one first detector being placed at about 180° with respect to the emission axis of the source, one second detector being placed at about 90° with respect to the emission axis of the source, one third detector being placed at about 45° with respect to the emission axis of the source, one fourth detector being placed at about 0° with respect to the emission axis of the source.

In a 52$^{nd}$ aspect according to any one of the preceding aspects, the detectors are configured to receive the signal emitted by the source radially along the normal section of the blood flow in the tube of the extracorporeal blood treatment apparatus.

In a 53$^{rd}$ aspect according to any one of the preceding aspects, the sensor further comprises a housing having one portion which is substantially counter-shaped to the tube of the extracorporeal blood treatment apparatus, each detector including a respective end placed at the counter-shaped portion facing the tube in a coupling condition of the hosing with the tube, in particular the signal emitter including an end placed at the counter-shaped portion facing the tube in a coupling condition of the hosing with the tube.

In a 54$^{th}$ aspect according to any one of the preceding aspects, the sensor further comprises a housing made of two or more pieces defining a through passage, the housing being configured to be coupled to the tube of the extracorporeal blood treatment apparatus, in particular to completely house a segment of the tube inside the through passage.

In a 55$^{th}$ aspect according to the preceding aspect, the through passage is counter-shaped to the outer shape of the tube segment of the extracorporeal blood treatment apparatus where blood is to flow.

In a 56$^{th}$ aspect according to any one of the preceding three aspects, the housing is configured for tight coupling with the outer surface of the tube segment.

In a 57$^{th}$ aspect according to any one of the preceding four aspects, the source includes a fiber optic having one end coupled with the signal emitter and the other end fixed to a housing having one portion which is substantially counter-shaped to the tube of the extracorporeal blood treatment apparatus, the other end of the fiber optic being placed at the counter-shaped portion and facing the tube in a coupling condition of the housing with the tube.

In a 58$^{th}$ aspect according to any one of the preceding aspects, at least one detector, and in particular all detectors, includes a fiber optic, one end being placed in correspondence of the tube, the other end being coupled to a receiver, in detail a photodiode receiver.

In a 59$^{th}$ aspect according to the preceding aspect, the end of the fiber optic in correspondence of the tube is fixed to a housing having one portion which is substantially counter-shaped to the tube of the extracorporeal blood treatment apparatus, the end of the fiber optic being placed at the counter-shaped portion and facing the tube in a coupling condition of the housing with the tube segment.

In a 60$^{th}$ aspect according to any one of the preceding two aspects, the sensor includes a printed circuit board with circuitry for transimpedance amplification, wherein the detectors include respective photodiode receivers connected to the printed circuit board, the circuitry for transimpedance amplification being a current-to-voltage converter and amplifying a current output of the detectors.

In a 61$^{st}$ aspect according to the preceding aspect, the printed circuit board include a lowpass filtering for filtering the signals exiting the circuitry for transimpedance amplification, in particular the cutoff frequency of the lowpass filter being about 30 Hz.

In a 62$^{nd}$ aspect according to any one of the preceding two aspects, the sensor includes a shielding case to prevent electromagnetic interference, the shielding case enclosing at least the printed circuit board with circuitry for transimpedance amplification and the lowpass filtering.

In a 63$^{rd}$ aspect an apparatus for extracorporeal blood treatment is provided comprising:
  a holder (71, 7, 73) of an extracorporeal blood circuit (60) of the type including a treatment unit (2), a withdrawal line 6) connected to an inlet of the treatment unit (2), and a return line (7) connected to an outlet of the same treatment unit (2), the extracorporeal blood circuit (60) comprising an extracorporeal segment (61), such as a tube segment;
  a control unit (10) for driving the extracorporeal blood treatment apparatus; and
  at least one non-invasive sensor (50) according to any one of the preceding aspects.

In a 64$^{th}$ aspect according to the preceding aspect, the controller (65) of the non-invasive sensor (50) is part of the control unit (10).

In a 65$^{th}$ aspect according to the preceding aspect 63, the controller (65) of the non-invasive sensor (50) is separate from the control unit (10).

In a 66$^{th}$ aspect according to any one of the preceding apparatus aspects, the apparatus comprises the extracorporeal blood circuit (60) mounted on said holder (71, 72, 73) and with said tube segment (61) received by said sensor (50), wherein said tube segment (61) is a tubular segment (61) of the blood withdrawal line or of the blood return line and wherein—when the sensor (50) is in an operative condition is configured to be positioned about and in contact with an external surface of said segment (61) of the extracorporeal blood circuit.

In a 67$^{th}$ aspect according to any one of the preceding apparatus aspects, a housing (51) of the sensor (50) comprises:
  a first housing part (51a) carrying respective detector ends, and
  a second housing part (51b);
wherein the first housing part (51a) and the second housing part (51b) are relatively movable the one relative to the other between a loading condition of said sensor (50), at which the housing (51) is open and said tube segment (61) may be inserted into the housing, and an operative condition of the sensor (50), at which the housing forms a longitudinal seat matching the shape of the outer surface of said tube segment (61), and
wherein—in correspondence of said operative condition—the detector ends face, and in particular contact, the tube segment (61) being radially directed towards the tube segment development axis;
optionally wherein the first housing part (51a) is pivotally coupled to the second housing part (51b).

In a 68$^{th}$ aspect according to any one of the preceding apparatus aspects, the apparatus comprises:
  the extracorporeal circuit (60) with said treatment unit (2) being of the type having a semi-permeable membrane (5) separating a secondary chamber (4) from a primary chamber of the same treatment unit (2);
  a preparation line (19) having one end configured for being connected to an inlet of a secondary chamber (4) of said treatment unit (2);
  a spent dialysate line (13) having one end configured for being connected to an outlet of said secondary chamber (4);
wherein the control unit (10) is configured for commanding execution of the following steps:
  causing flow of a patient's blood in the extracorporeal blood circuit at a blood flow rate ($Q_b$), causing a fresh treatment liquid to flow in the preparation line (19) towards the secondary chamber (4) at a flow rate ($Qd_{in}$);

causing a used treatment liquid to flow in the spent dialysate line (13) at a flow rate ($Qd_{out}$);

receiving one or more values related to the conductivity ($\sigma_{in}$) or to the concentration of a substance ($Na_{in}$) of the fresh treatment liquid flowing in the preparation line (19);

receiving one or more measured values related to the conductivity ($\sigma_{out}$) or to the concentration of said substance ($Na_{out}$) in the used treatment liquid flowing in the spent dialysate line (13);

computing at least one value of a parameter (D, K·t) indicative of the effectiveness of the extracorporeal blood treatment based on:

said one or more measured values related to the conductivity ($\sigma_{out}$) or to the concentration of said substance ($Na_{out}$) of the used treatment liquid;

one or more values of the conductivity ($\sigma_{in}$) or to the concentration of said substance ($Na_{in}$) of the fresh treatment liquid;

said calculated value of the conductivity ($\sigma_{pl}$) or of the concentration ($Na_{pl}$) of said substance in blood flowing through said segment (61) of the extracorporeal blood circuit;

at least one of: said flow rate ($Qd_{in}$) of fresh treatment liquid and said flow rate ($Qd_{out}$) of used treatment liquid.

In a 69$^{th}$ aspect according to any one of the preceding apparatus aspects, the apparatus comprises:

the extracorporeal circuit (60) with said treatment unit (2) being of the type having a semi-permeable membrane (5) separating a secondary chamber (4) from a primary chamber of the same treatment unit (2);

a preparation line (19) having one end configured for being connected to an inlet of a secondary chamber (4) of said treatment unit (2);

a spent dialysate line (13) having one end configured for being connected to an outlet of said secondary chamber (4);

wherein the apparatus comprises at least two of said non-invasive sensors (50) such that a first tube segment (61) of the blood withdrawal line is received by a housing (51) of a first of said two sensors (50) and a second tube segment (61) of the blood return line is received by a housing (51) of a second of said two sensors, and wherein the control unit is connected to each sensor (50) and configured for:

causing flow of a patient's blood in the extracorporeal blood circuit at a blood flow rate ($Q_b$), causing a fresh treatment liquid to flow in the preparation line (19) towards the secondary chamber (4) at a flow rate ($Qd_{in}$);

causing a used treatment liquid to flow in the spent dialysate line (13) at a flow rate ($Qd_{out}$);

receiving one or more values related to the conductivity ($\sigma_{in}$) or to the concentration of a substance ($Na_{in}$) of the fresh treatment liquid flowing in the preparation line (19);

receiving or calculating a value of the conductivity ($\sigma_{pl,in}$) or of the concentration ($Na_{pl,in}$) of said substance in the blood flowing inside said first segment (61) and a value of the conductivity ($\sigma_{pl,out}$) or of the concentration ($Na_{pl,out}$) of said substance in the blood flowing inside said second segment (61), computing at least one value of a parameter (D, K·t) indicative of the effectiveness of the extracorporeal blood treatment based on:

said one or more values of the conductivity ($\sigma_{in}$) or to the concentration of said substance ($Na_{in}$) of the fresh treatment liquid;

said value of conductivity ($\sigma_{pl,in}$) or of the concentration ($Na_{pl,in}$) of said substance in the blood flowing inside said first segment (61) and said value of conductivity ($\sigma_{pl,out}$) or of the concentration ($Na_{pl,out}$) of said substance in the blood flowing inside said second segment (61), said blood flow rate ($Q_b$).

In a 70$^{th}$ aspect according to any one of the preceding two aspects, the step of causing a fresh treatment liquid to flow in the preparation line (19) comprises the sub-step of maintaining—at least for a time interval (T) during which the measurements of conductivity or concentration used for the purpose of said computation of at least one value of a parameter (D, K·t) indicative of the effectiveness of the extracorporeal blood treatment take place—the concentration of the substance ($Na_{in}$) or the conductivity ($\sigma_{in}$) in the fresh treatment liquid constant at a set value which is used for computing the at least one value of a parameter (D, K·t) indicative of the effectiveness of the extracorporeal blood treatment, and wherein at least during said time interval (T) the control unit is configured to keep constant the flow rate ($Qd_{in}$) of fresh treatment liquid in the preparation line (19), the flow rate ($Q_b$) of patient's blood in the extracorporeal blood circuit, and the flow rate ($Q_F$) of ultrafiltration flow through the semipermeable membrane.

In a 71$^{st}$ aspect according to any one of the preceding three aspects, the parameter (D, K·t) indicative of the effectiveness of the extracorporeal blood treatment is dialysance (D) for said substance which is calculated using the one of the following formulas:

$$D = \frac{Qd_{in} \times (\sigma_{in} - \sigma_{out}) + Q_F \times \sigma_{out}}{\sigma_{in} - \sigma_{pl}}$$

or $$D = \frac{Qd_{in} \times (Na_{in} - Na_{out}) + Q_F \times Na_{out}}{Na_{in} - Na_{pl}}$$

or $$D = \frac{Qb_{in} \times (\sigma_{pl,in} - \sigma_{pl,out}) + Q_F \times \sigma_{pl,out}}{\sigma_{pl,in} - \sigma_{in}}$$

or $$D = \frac{Qb_{in} \times (Na_{pl,in} - Na_{pl,out}) + Q_F \times Na_{pl,out}}{Na_{pl,in} - Na_{in}}$$

wherein

| | |
|---|---|
| D | Treatment unit dialysance |
| $Qd_{in}$ | Fresh dialysis fluid flow rate at the treatment unit inlet |
| $Q_F$ | Ultrafiltration flow rate |
| $\sigma_{in}$ | Inlet dialysate conductivity at the inlet of the filtration unit |
| $\sigma_{Out}$ | Outlet dialysate conductivity at the outlet of the filtration unit |

-continued

| | |
|---|---|
| $\sigma_{pl}$ | Plasmatic conductivity |
| $Na_{In}$ | Inlet dialysate sodium concentration at the inlet of the filtration unit |
| $Na_{out}$ | Outlet dialysate sodium concentration at the outlet of the filtration unit |
| $Na_{Pl}$ | Plasma sodium concentration in tube segment |
| $\sigma_{pl,\,in}$ | Plasmatic conductivity at the inlet of the filtration unit |
| $\sigma_{pl,\,out}$ | Plasmatic conductivity at the outlet of the filtration unit |
| $Na_{Pl,\,in}$ | Plasma sodium concentration in tube segment upstream the filtration unit |
| $Na_{Pl,\,out}$ | Plasma sodium concentration in tube segment downstream the filtration unit |

In a 72$^{nd}$ aspect according to any one of the preceding apparatus aspects, the apparatus comprises an on line fluid preparation section (100) connectable to the extracorporeal blood circuit (60) and configured for preparing priming fluid.

In a 73$^{rd}$ aspect according to any one of the preceding apparatus aspects, the apparatus comprises said treatment unit (2), wherein:
the preparation line (19) has one end connected to an inlet of the secondary chamber (4) of the treatment unit (2), the spent dialysate line (13) has one end connected to the outlet of said secondary chamber (4),
a blood withdrawal line (6) is connected at an inlet of the primary chamber (3) and
a blood return line (7) is connected at an outlet of the primary chamber (3).

In a 74$^{th}$ aspect a process for determining at least one property of blood and/or an auxiliary parameter of blood flowing in an extracorporeal segment (61), e.g. a tube segment, of an extracorporeal blood treatment apparatus is provided, wherein a non-invasive sensor (50), in particular a blood volume sensor, comprises:
at least one source (53) for directing a signal towards the blood along an emission axis (54);
a plurality of detectors (57) for receiving the signal emitted by said source (53) after at least partially passing through the blood flowing in the segment (61) and emitting respective output signals related to the received signal, the process including:
receiving the respective output signals from the plurality of detectors (57); and
determining a value of said property of blood based on the output signals,
in particular wherein said property of blood includes blood volume variation or hemoglobin concentration or a parameter directly related to blood volume variation or hemoglobin concentration.

In a 75$^{th}$ aspect according to the preceding aspect, the process comprises determining a value of an auxiliary blood parameter, said auxiliary parameter is plasma conductivity ($\sigma_{pl}$), a plasma conductivity-related parameter, concentration of at least one substance in the blood ($Na_{pl}$), e.g. sodium, and a concentration-related parameter of at least one substance in the blood.

In a 76$^{th}$ aspect according to any one of the preceding process aspects, the process comprises determining a value of the property of blood based on the output signals from the plurality of detectors (57).

In a 77$^{th}$ aspect according to any one of the preceding process aspects, the process comprises determining a time variation of said auxiliary blood parameter based on the output signals.

In a 78$^{th}$ aspect according to any one of the preceding process aspects, the process comprises determining a time variation of said property of blood based on the output signals.

In a 79$^{th}$ aspect according to any one of the preceding process aspects, the process comprises receiving values for a sodium concentration ($Na_{in}$) of an inlet dialysis fluid flowing in a preparation line (19) of the extracorporeal blood treatment apparatus (1), and determining the value of said auxiliary blood parameter based on the inlet dialysis fluid sodium concentration ($Na_{in}$).

In an 80$^{th}$ aspect according to any one of the preceding process aspects, the process comprises receiving values for a sodium concentration ($Na_{in}$) of an inlet dialysis fluid flowing in a preparation line (19) of the extracorporeal blood treatment apparatus (1), and determining the value of said property of blood based on the inlet dialysis fluid sodium concentration ($Na_{in}$).

In an 81$^{st}$ aspect according to any one of the preceding process aspects, the process comprises receiving values for a conductivity ($\sigma_{in}$) of an inlet dialysis fluid flowing in a preparation line (19) of the extracorporeal blood treatment apparatus (1), and determining the value of said auxiliary blood parameter based on the inlet dialysis fluid conductivity ($\sigma_{in}$).

In an 82$^{nd}$ aspect according to any one of the preceding process aspects, the process comprises receiving values for a conductivity ($\sigma_{in}$) of an inlet dialysis fluid flowing in a preparation line (19) of the extracorporeal blood treatment apparatus (1), and determining the value of said property of blood based on the inlet dialysis fluid conductivity ($\sigma_{in}$).

In an 83$^{rd}$ aspect according to any one of the preceding process aspects, the process comprises receiving values for a conductivity ($\sigma_{out}$) of an outlet dialysis fluid flowing in a spent dialysate line (13) of the extracorporeal blood treatment apparatus (1), and determining the value of said auxiliary blood parameter based on the outlet dialysis fluid conductivity ($\sigma_{out}$).

In an 84$^{th}$ aspect according to any one of the preceding process aspects, the process comprises receiving values for a conductivity ($\sigma_{out}$) of an outlet dialysis fluid flowing in a spent dialysate line (13) of the extracorporeal blood treatment apparatus (1), and determining the value of said property of blood based on the outlet dialysis fluid conductivity ($\sigma_{out}$).

In an 85$^{th}$ aspect according to any one of the preceding process aspects, the process comprises using a state-space mathematical modeling for determining said property of blood and/or said auxiliary blood parameter, wherein the state-space mathematical modeling includes the following equations:

$$\Delta \dot{R}BV(t) = 0 \qquad (6)$$

$$Na\dot{}_{Pl}(t) = \frac{Na_{In}(t) - Na_{Pl}(t)}{\tau_{Diff}} \qquad (7)$$

wherein

| | |
|---|---|
| $\Delta \dot{R}BV(t)$ | Differential relative blood volume |
| $Na\dot{}_{Pl}(t)$ | Differential plasma sodium concentration in tube segment 61 at instant t |
| $Na_{Pl}(t)$ | Plasma sodium concentration in tube segment 61 at instant t |

| | |
|---|---|
| $Na_{In}$ (t) | Inlet dialysate sodium concentration at instant t at the inlet of the filtration unit |
| $\tau_{Diff}$ | Diffusion time |

In an 86th aspect according to any one of the preceding process aspects, the process comprises determining both said property of blood and an auxiliary blood parameter based on the output signals from the plurality of detectors (57) using a mathematical equation linearly combining values of the property of blood, of the auxiliary blood parameter and of the output signals.

In an 87th aspect according to any one of the preceding process aspects, the process comprises determining both said property of blood and an auxiliary blood parameter based on the output signals from the plurality of detectors (57) using the following mathematical equation:

$$\Delta RP_i(t) = G_{Opt,i,1} \cdot \Delta RBV(t) + G_{Opt,i,2} \cdot Na_{Pl}(t) \cdot G_{Opt,i,3} \quad (8)$$

wherein

| | |
|---|---|
| $\Delta RP_i$ (t) | Optical output of detector i |
| $G_{Opt, i, 1}$ | Coefficients 1 to 3 for the output signal from i-detector |
| $G_{Opt, i, 2}$ | |
| $G_{Opt, i, 3}$ | |
| $\Delta RBV$ (t) | Relative blood volume |
| $Na_{Pl}$ (t) | Plasma sodium concentration in tube segment 61 at instant t |

In an 88th aspect according to any one of the preceding process aspects, the process comprises using a state-space mathematical modeling for determining said property of blood and/or said auxiliary blood parameter, wherein in a by-pass condition of the extracorporeal blood treatment apparatus where the inlet dialysis fluid is not routed into, and by-passes, a filtration unit, the state-space mathematical modeling includes the following equations:

$$\Delta \dot{R}BV(t) = 0 \quad (6)$$

$$\dot{Na}_{Pl}(t) = 0 \quad (13)$$

wherein

| | |
|---|---|
| $\Delta \dot{R}BV$ (t) | Differential relative blood volume |
| $\dot{Na}_{Pl}$ (t) | Differential plasma sodium concentration in tube segment 61 at instant t |

In an 89th aspect according to any one of the preceding process aspects, the process comprises determining the auxiliary blood parameter also based on an outlet dialysis fluid conductivity ($\sigma_{out}$) modeled as an average, in particular a weighted average, of an inlet dialysis fluid conductivity ($\sigma_{in}$) and of a plasma conductivity ($\sigma_{pl}$), wherein the outlet dialysis fluid conductivity ($\sigma_{out}$) is the conductivity of a dialysis fluid flowing in a spent dialysate line (13) of the extracorporeal blood treatment apparatus, the inlet dialysis fluid conductivity ($\sigma_{in}$) is the conductivity of a dialysis fluid flowing in a preparation line (19) of the extracorporeal blood treatment apparatus and the plasma conductivity ($\sigma_{pl}$) being the conductivity of the blood flowing in the tube segment (61).

In a 90th aspect according to any one of the preceding process aspects, the process comprises determining the auxiliary blood parameter also based on the following mathematical relationship:

$$\sigma_{Out}(t) = G_{Mix} \cdot \sigma_{Pl}(t) + (1 - G_{Mix}) \cdot \sigma_{In}(t - \tau_{Delay}) \quad (11)$$

wherein

| | |
|---|---|
| $\sigma_{in}(t)$ | Inlet dialysate conductivity at instant t at the inlet of the filtration unit |
| $\sigma_{Out}(t)$ | Outlet dialysate conductivity at instant t at the outlet of the filtration unit |
| $\sigma_{pl}(t)$ | Plasmatic conductivity in tube segment 61 at instant t |
| $G_{Mix}$ | Weighing coefficient, e.g. equal to $\frac{D}{J_D}$ |
| Delay $\tau_{Delay}$ | Delay time to account for the propagation time of changes in the inlet dialysate composition across the hydraulic circuit |

In a 91st aspect according to any one of the preceding process aspects, the process comprises determining the auxiliary blood parameter also based on a plasma conductivity ($\sigma_{pl}$), being the conductivity of the blood flowing in the tube segment (61).

In a 92nd aspect according to any one of the preceding process aspects, the process comprises determining the auxiliary blood parameter also based on the following mathematical relationship:

$$\sigma_{Pl}(t) = G_{Na,Gain} \cdot Na_{Pl}(t) + G_{Na,Offset} \quad (12)$$

wherein

| | |
|---|---|
| $\sigma_{pl}$ (t) | Plasmatic conductivity in tube segment 61 at instant t |
| $G_{Na, Gain}$ | Constant coefficient |
| $G_{Na, Offset}$ | Constant coefficient |
| $Na_{Pl}$ (t) | Plasma sodium concentration in tube segment 61 at instant t |

In a 93rd aspect according to any one of the preceding process aspects, the process comprises using a Kalman filter for determining said property of blood and/or said auxiliary blood parameter.

Glossary

The following terms are consistently used throughout the equations provided in the following description of the detailed working of the extracorporeal blood treatment apparatus.

| | | |
|---|---|---|
| Qb | Blood flow rate | ml/min |
| $Qd_{out}$ | Effluent flow rate | ml/min |
| $Q_F$ | Ultrafiltration flow rate | ml/min |
| $Q_{rep1}$ | Replacement flow rate along infusion line 15 | ml/min |
| $Qd_{in}$ | Fresh dialysis fluid flow rate at the treatment unit inlet | ml/min |
| $V_B(t)$ | Absolute blood volume at instant t | L |
| $V_{B,0}$ | Absolute blood volume at instant 0 (blood volume at treatment starting) | L |
| $J_{UF}(\tau)$ | Ultrafiltration rate | L/h |

| | | |
|---|---|---|
| $J_{Ref}(\tau)$ | Refilling rate | L/h |
| $J_D$ | Dialysis flow rate | L/h |
| $\Delta RBV(t)$ | Relative blood volume | |
| $\Delta \dot{R}BV(t)$ | Differential relative blood volume | |
| $Na_{Pl}(t)$ | Plasma sodium concentration in tube segment 61 at instant t | mM |
| $Na_{Ref}(t)$ | Refilling fluid sodium concentration at instant t | mM |
| $Na_{In}(t)$ | Inlet dialysate sodium concentration at instant t at the inlet of the filtration unit | mM |
| $Na_{out}(t)$ | Outlet dialysate sodium concentration at instant t at the outlet of the filtration unit | mM |
| $Na_{Pl,in}$ | Plasma sodium concentration in tube segment upstream the filtration unit | mM |
| $Na_{Pl,out}$ | Plasma sodium concentration in tube segment downstream the filtration unit | mM |
| $K_{Diff}$ | Semipermeable membrane diffusion coefficient for sodium | |
| $Na_{Pl}(t)$ | Differential plasma sodium concentration at instant t | |
| $\sigma_{in}(t)$ | Inlet dialysate conductivity at instant t at the inlet of the filtration unit | mS/cm |
| $\sigma_{Out}(t)$ | Outlet dialysate conductivity at instant t at the outlet of the filtration unit | mS/cm |
| $\sigma_{pl}(t)$ | Plasmatic conductivity at instant t | mS/cm |
| $\sigma_{pl,in}(t)$ | Plasmatic conductivity at the inlet of the filtration unit | mS/cm |
| $\sigma_{pl,out}(t)$ | Plasmatic conductivity at the outlet of the filtration unit | mS/cm |
| $\Delta RP_i(t)$ | Optical output of detector i | |
| $V_{Out,i}(t)$ | (Recorded analog voltage output at instant t; i indicates the output channel of detector i | V |
| $V_{Out,i}(0)$ | Recorded analog voltage output at instant 0; i indicates the output channel of detector i | V |
| $\tau_{Diff}$ | Diffusion time | s |
| $G_{Opt}$ | 4 × 3 matrix containing weighting coefficients for all channels of the signal detectors | |
| D | Treatment unit dialysance | ml/min |
| $G_{Mix}$ | Equal to $\dfrac{D}{J_D}$ | |
| $G_{Na,Gain}$ | Coefficient of linear equation 12 | |
| $G_{Na,Offset}$ | Coefficient of linear equation 12 | |
| $\tau_{Delay}$ | Delay time to account for the propagation time of changes in the inlet dialysate composition across the hydraulic circuit | s |
| $k_{Delay}$ | Discrete version of $\tau_{Delay}$ | s |
| k | Time step (e.g. 1 s) | s |

DESCRIPTION OF THE DRAWINGS

Aspects of the invention are shown in the attached drawings, which are provided by way of non-limiting example, wherein:

FIG. 3b is a further scheme of the measurement system to reveal some components of the circuit;

FIG. 7 is an illustration of the blood pool model used for the computation of reference signals;

FIG. 8 illustrates the relationship between input signals, state variables and output signals, the dotted lines representing connections which are unreliable during bypass mode;

FIG. 9 represents a transition between different filter versions for bypass condition management;

FIGS. 10a to 10f show examples of state estimation results, wherein FIGS. 10a, 10b and 10c show ΔRBV estimation for three different experimental sessions and FIGS. 10d, 10e and 10f show $Na_{Pl}$ estimation for the corresponding experiments; the dotted black line displaying the reference data, the light grey solid line displays the Kalman-based state variable estimation, the dashed black lines display the estimation confidence interval and the dark grey solid lines display the intervals of the estimation performed in bypass mode;

DETAILED DESCRIPTION

Figure 1:
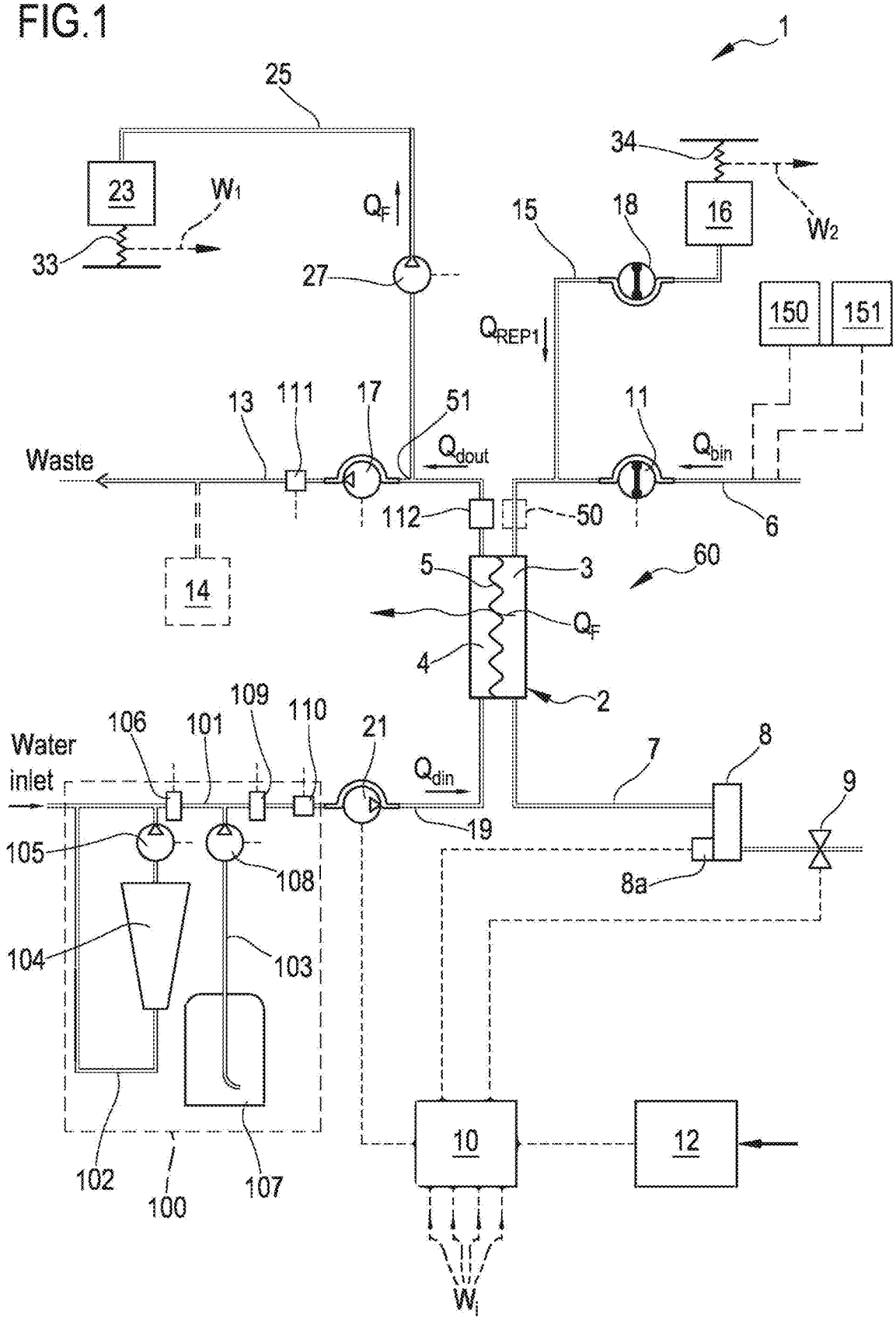
FIG. 1 shows a schematic diagram of a blood treatment apparatus according to one aspect of the invention.
Figure 2:
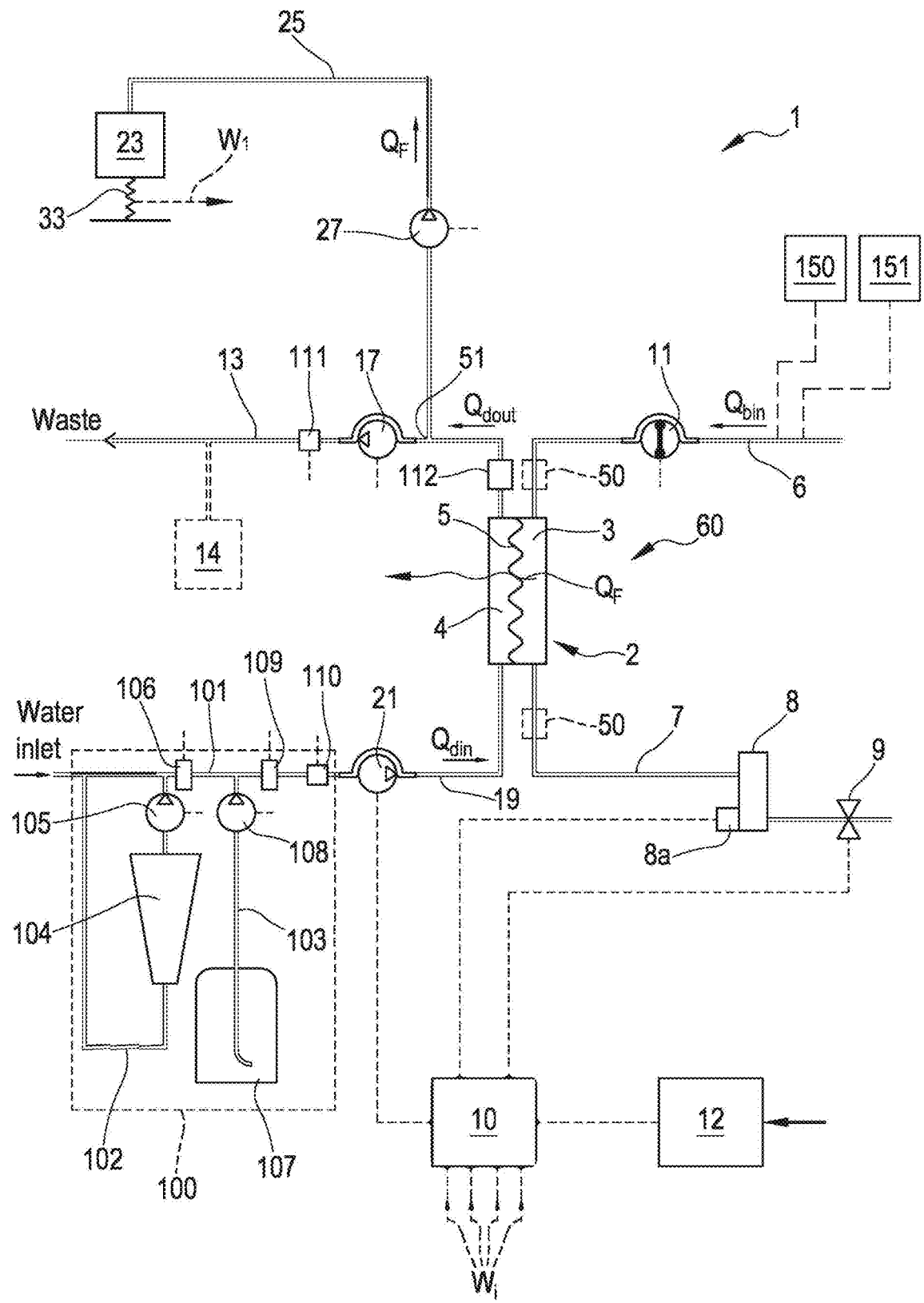
FIG. 2 shows a schematic diagram of an alternative embodiment of a blood treatment apparatus according to another aspect of the invention.

Non-limiting embodiments of an apparatus 1 for extracorporeal treatment of blood—which may implement innovative aspects of the invention—are shown in FIGS. 1 and 2. In below description and in FIGS. 1 and 2 same components are identified by same reference numerals.

The apparatus 1 includes at least one sensor 50 which may be configured to determine the value of one or more blood or plasma parameters FIG. 1 shows an apparatus 1 configured to deliver any one of treatments like ultrafiltration, hemodialysis and hemodiafiltration, while FIG. 2 shows an apparatus configured to deliver hemodialysis or ultrafiltration treatments.

The apparatus 1 comprises a treatment unit 2 (such as an hemofilter, an ultrafilter, an hemodiafilter, a dialyzer, a plasmafilter and the like) having a primary chamber 3 and a secondary chamber 4 separated by a semi-permeable membrane 5; depending upon the treatment, the membrane 5 of the treatment unit 2 may be selected to have different properties and performances.

Figure 11:
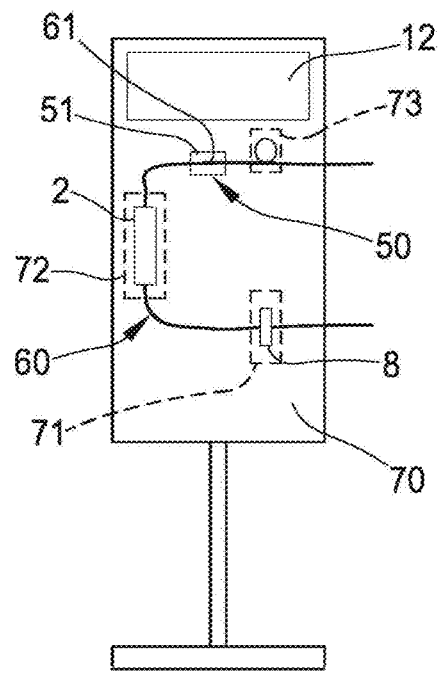
FIG. 11 shows a schematic front view of a cabinet structure for the apparatus of FIG. 1 or 2.

A blood withdrawal line 6 is connected to an inlet of the primary chamber 3, and a blood return line 7 is connected to an outlet of the primary chamber 3. The blood withdrawal line 6, the primary chamber 3, and the blood return line 7 are part of an extracorporeal blood circuit which is globally identified with reference number 60 in FIGS. 1 and 2. In use, the blood withdrawal line 6 and the blood return line 7 are connected to a needle or to a catheter or other access device (not shown) which is then placed in fluid communication with the patient vascular system, such that blood may be withdrawn through the blood withdrawal line, flown through the primary chamber and then returned to the patient's vascular system through the blood return line. An air separator, such as a bubble trap 8 may be present on the blood return line; the extracorporeal blood circuit is supported by one or more holders provided, in a conventional manner, by the support framework 70 of the apparatus 1. For instance, as shown in FIG. 11, the extracorporeal blood circuit 60 may be supported by a holder 71 holding the bubble trap, by a holder 72 holding the treatment unit 2, and by a holder 73 located in correspondence of the blood pump.

A safety clamp 9 controlled by a control unit 10 may be present on the blood return line downstream the bubble trap 8. A bubble sensor 8a, for instance associated to the bubble trap 8 or coupled to a portion of the line 7 between bubble trap 8 and clamp 9 may be present: if present, the bubble sensor is connected to the control unit 10 and sends to the control unit signals for the control unit to cause closure of the clamp 9 in case one or more bubbles above certain safety thresholds are detected. The blood flow through the blood lines may be controlled by a blood pump 11, for instance a peristaltic blood pump, acting either on the blood withdrawal line (as shown in FIG. 1) or on the blood return line. An operator may enter a set value for the blood flow rate Qb: the control unit 10, during treatment, is configured to control the blood pump based on the set blood flow rate. It is noted that the control unit 10 may also be connected to a user interface 12, for instance a graphic user interface, which receives operator's inputs (such as, inter alia, the set value for the blood flow rate) and displays the apparatus outputs. For instance, the graphic user interface 12 may include a touch screen for both displaying outputs and allowing user entries, or a display screen and hard keys for entering user's inputs, or a combination thereof.

A spent dialysate line 13 configured for evacuating an effluent fluid coming from the secondary chamber 4 is connected, at one end, to an outlet of the secondary chamber 4 and, at its other end, to a waste which may be a discharge conduit or an effluent fluid container 14 (dashed lines in FIGS. 1 and 2) collecting the fluid extracted from the secondary chamber. An effluent fluid pump 17 operates on the spent dialysate line 13 under the control of control unit 10 to regulate the flow rate $Qd_{out}$ of effluent fluid through the spent dialysate line. The net ultrafiltration (i.e. the net fluid removed from the blood across the semipermeable membrane of the treatment unit 2 may be determined by the flow rate difference between a dialysis fluid pump 21 on the fresh dialysis fluid line 19 and the effluent fluid pump 17. Alternatively (or in combination) the apparatus may also include an ultrafiltration line 25 branching off the spent dialysate line 13 and provided with a respective ultrafiltration pump 27 also controlled by control unit 10 to cause a flow rate $Q_F$ along the ultrafiltration line. The embodiment of FIG. 1 presents a pre-dilution fluid line 15 connected to the blood withdrawal line: this line 15 supplies replacement fluid from an infusion fluid container 16 connected at one end of the pre-dilution fluid line. Although FIG. 1 shows a container 16 as source of infusion fluid, this should not be interpreted in a limitative manner: indeed, the infusion fluid may alternatively come from an on line preparation section. Note that, alternatively to the pre-dilution fluid line, the apparatus of FIG. 1 may include a post-dilution fluid line (not shown in FIG. 1) connecting an infusion fluid container or an on line preparation section of infusion solution to the blood return line. Finally, as a further alternative (not shown in FIG. 1) the apparatus of FIG. 1 may include both a pre-dilution and a post infusion fluid line: in this case each infusion fluid line may be connected to a respective infusion fluid container or may receive infusion fluid from a same source of infusion fluid such as a same infusion fluid container or an online preparation section. In case the infusion fluid is prepared online, the source of infusion fluid may be an online preparation section part of the apparatus 1 (i.e. as the online preparation section 100 described herein below) or a distinct device analogous to section 100 and connected to the infusion line or lines and configured for supplying fluid to the post and/or pre dilution lines. Furthermore, an infusion pump 18 operates on the infusion line 15 to regulate the flow rate $Q_{repl}$ through the infusion line 15. Note that in case of two infusion lines (pre-dilution and post-dilution) each infusion line may be provided with a respective infusion pump.

The apparatus of FIG. 1, further includes a fluid preparation line 19 connected at one end with a water inlet and at its other end with the inlet of the secondary chamber 4 of the filtration unit for supplying fresh treatment liquid to the secondary chamber 4. A dialysis fluid pump 21 works on the fluid preparation line under the control of said control unit 10, to supply fluid from a source of fresh treatment liquid (such as a container or the section 100 for online preparing fresh dialysis liquid) to the secondary chamber at a flow rate $Qd_{in}$.

In the example of FIGS. 1 and 2, the line 19 links the hemodialyzer or hemodiafilter 2 to online preparation section 100, which is configured for preparing the dialysis liquid: section 100 comprises a main line 101, the upstream end of which is designed to be connected to a supply of water. A first secondary line 102 and a second secondary line 103 are connected to the main line 101 and are configured to at least supply the necessary quantity of a buffer and the necessary quantity of electrolytes. The first secondary line 102, which may be looped back onto the main line 101, is configured for fitting a first container 104, such as a bag or cartridge or other container, containing a buffer. Line 102 is furthermore equipped with a first metering pump 105 for dosing the buffer into the fresh treatment liquid: as shown in FIG. 1 the pump may be located downstream of the first container 104. The operation of the pump 105 may be controlled by the control unit 10 based upon the comparison between: 1) a set point value for the buffer concentration of the solution forming at the junction of the main line 101 and the first secondary line 102, and 2) the value of the buffer concentration of this mixture measured by through a first probe 106 located either in the first secondary line downstream the first container 104 or in the main line 101 immediately downstream of the junction between the main line 101 and the first secondary line 102. Furthermore, the free end of the second secondary line 103 is intended to receive fluid from second container 107 containing a concentrated saline solution, e.g. electrolytes such as sodium chloride, calcium chloride, magnesium chloride and potassium chloride. In a variant also the second secondary line 103 may be looped back onto the main line 101. Moreover, it is possible envisaging a plurality of independent second secondary lines 103 in the case one wishes to feed separate electrolytes or electrolyte compositions from respective containers. Note that the second secondary line 103 is equipped with a second metering pump 108 for dosing electrolytes into the fresh treatment liquid; operation of the second metering pump depends on the comparison between 1) a conductivity setpoint value or an electrolyte concentration setpoint value for the solution forming at the junction of the main line 101 with the second secondary line 103, and 2) the value of the conductivity or electrolyte concentration of this solution measured by through a second probe 109 located either in the second secondary line downstream of second container 107 or in the main line 101 immediately downstream of the junction between the main line 101 and the secondary line 103. Note that the specific nature of the concentrates contained in containers 104 and 107 may be varied depending upon the circumstances and of the type of fresh treatment fluid to be prepared. Moreover, the nature and the position of the first and second probes may depend upon the type of buffer used, the type of electrolyte concentrate(s) adopted and upon the specific configuration of the circuit formed by the main line and the secondary lines. Furthermore, as already mentioned, more than two secondary lines, with respective concentrate containers and respective metering pumps may be in case a plurality of different type of substances need to be added for the preparation of the fresh treatment fluid.

The second probe is generally a conductivity meter configured for measuring the dialysis fluid conductivity $\sigma_{in}$ upstream the filtration unit 2. Of course, dialysis fluid conductivity $\sigma_{in}$ is set by the operator or set and controlled by the apparatus during treatment. Correspondingly, the apparatus include a further conductivity meter 112 placed on the spent dialysate line 13 to sense conductivity Gout of the dialysis fluid downstream the filtration unit 2. Both conductivity meters 109 and 112 provide the respective measuring signal to the apparatus control unit 10.

The embodiment of FIG. 2 shows an alternative apparatus 1 designed for delivering any one of treatments like hemodialysis and ultrafiltration. In the apparatus shown in FIG. 2 the same components described for the embodiment of FIG. 1 are identified by same reference numerals and thus not described again. In practice, differently from the hemodiafiltration apparatus of FIG. 1, the apparatus of FIG. 2 does not present any infusion line.

In each one of the above described embodiments, flow sensors 110, 111 (either of the volumetric or of the mass type) may be used to measure flow rate in each of the lines. Flow sensors are connected to the control unit 10. In the example of FIG. 1, where the infusion line 15 and the ultrafiltration line 25 lead to a respective container or bag 16, 23, scales may be used to detect the amount of fluid delivered or collected. For instance, the apparatus of FIG. 1 includes a first scale 33 operative for providing weight information $W_1$ relative to the amount of the fluid collected in the ultrafiltration container 23 and a second scale 34 operative for providing weight information $W_2$ relative to the amount of the fluid supplied from infusion container 16. In the embodiment of FIG. 2, the apparatus includes a first scale 33 operative for providing weight information $W_1$ relative to the amount of the fluid collected in the ultrafiltration container 23. The scales are all connected to the control unit 10 and provide said weight information $W_j$ for the control unit to determine the actual quantity of fluid in each container as well as the actual flow rate of fluid supplied by or received in each container.

In the example of FIGS. 1 and 2, in order to control the fluid balance between the quantity of fluid supplied to the secondary chamber 4 and the quantity of fluid extracted from the secondary chamber, the flow sensors 110, 111 positioned on the fresh dialysate line and on the spent dialysate line 13 provide the control unit 10 with signals indicative of the flow of fluid through the respective lines and the scale or scales provide weight information which allow the control unit to derive the flow rate through the ultrafiltration line 25 and, if present, through the infusion line 15. The control unit is configured to control at least pumps 17, 21 and 27 (in case of FIG. 3 also pump 18) to make sure that a prefixed patient fluid removal is achieved in the course of a prescribed treatment time, as required by the prescription provided to the control unit, e.g. via user interface 12. Note that other fluid balance systems may be used: for instance in case the apparatus includes a container as source of fresh treatment fluid and a container to collect waste, then scales may be used to detect the amount of fluid delivered or collected by each container and then inform the control unit accordingly. As a further alternative, systems based on volumetric control may be used where the preparation line 19 and the spent dialysate line 13 are connected to a balance chamber system assuring that—at each instant—the quantity of liquid flowing into line 19 is identical to the quantity of fluid exiting from line 13.

From a structural point of view one or more, containers 104, 107, 16, 23 may be disposable plastic containers. The blood lines 6, 7 lines and the filtration unit may also be plastic disposable components which may be mounted at the beginning of the treatment session and then disposed of at the end of the treatment session. Pumps, e.g. peristaltic pumps or positive displacement pumps, have been described as means for regulating fluid flow through each of the lines; however, it should be noted that other flow regulating means may alternatively be adopted such as for example valves or combinations of valves and pumps. The scales may comprise piezoelectric sensors, or strain gauges, or spring sensors, or any other type of transducer able to sense forces applied thereon.

Measurement System

According to an aspect of the invention, the apparatus 1 includes at least one blood or plasma parameter sensor 50, which is configured to be positionable in correspondence of at least one segment 61 of the extracorporeal blood circuit 60.

The sensor 50 is a non-invasive sensor, i.e. it does not enter into contact with the blood flowing inside the extracorporeal blood circuit 60 and in particular it is applied on the outside of a segment of an extracorporeal blood treatment apparatus. In the following the segment of the extracorporeal blood treatment apparatus referred to will be, in a non-limiting approach, a tube segment. From the structural point of view, the sensor 50 includes a plastic housing 51 only schematically represented in the annexed drawings. The housing 51 is designed to tightly couple to the blood line segment 61 of the extracorporeal blood circuit 60 where the blood or plasma parameters need to be measured. The housing 51 may be a standalone body or may be attached to or be part of the support framework 70 of the apparatus 1. For instance, FIG. 11 schematically shows the housing 51 attached to the front panel of the support framework 70 and configured to receive at least one (in the examples of the drawings only one) segment 61 of the extracorporeal blood circuit. To this aim, the housing 51 may be counter-shaped directly to a portion of a blood line tubing, namely to a circular cross section segment of flexible transparent plastic tubing of a blood withdrawal line 6 or blood return line 7. The housing may be an open-and-close housing defining an inside through passage 52 destined to receive the tube of the blood circuit.

Figure 3:
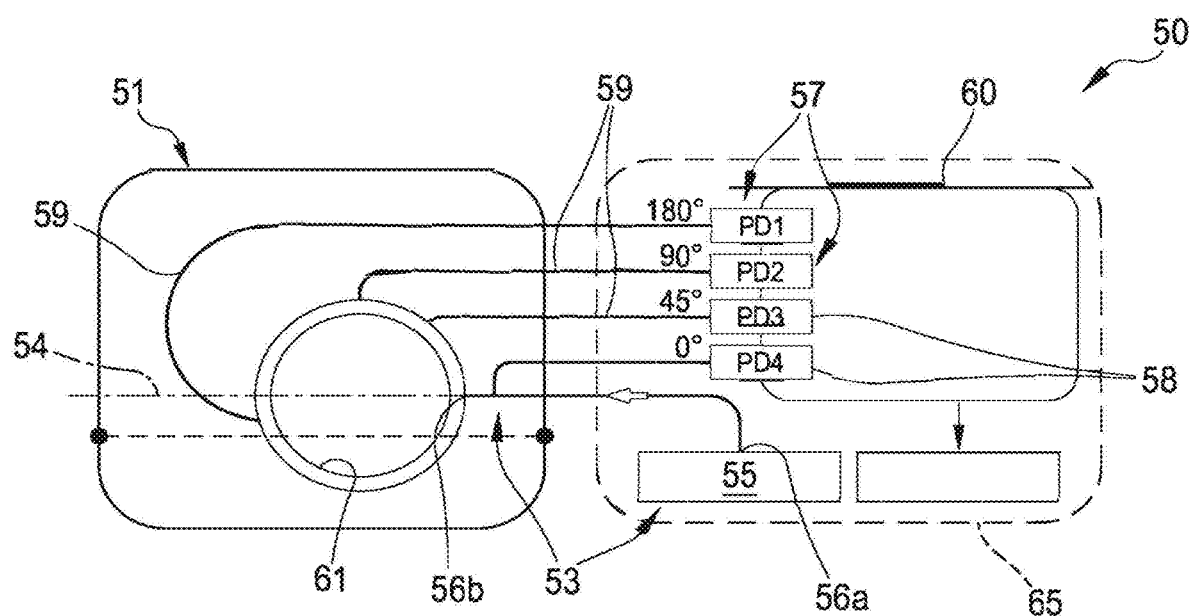
FIG. 3 is a schematic view of the measurement system according to one embodiment of the present invention.
Figure 3A:
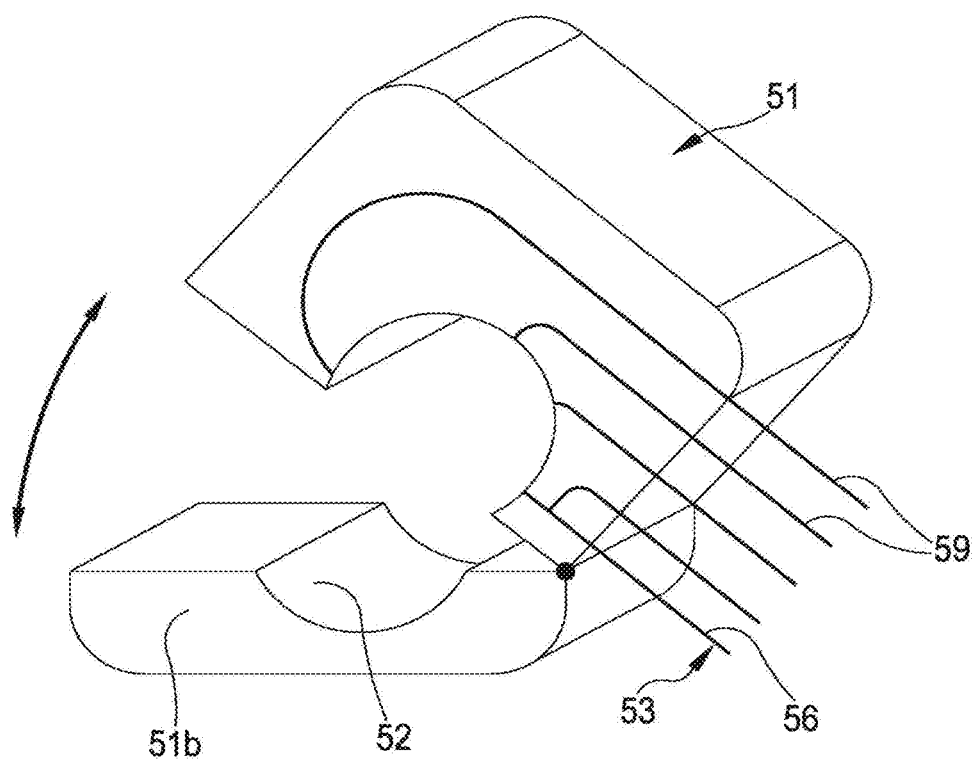
FIG. 3a shows a schematic perspective of a housing for receiving a tube segment having blood flowing therein.

Notably, the housing 51 may be made of two or more parts 51*a*, 51*b* either separate or joined, e.g. hinged, together so to define an uncoupled configuration (see FIG. 3*a*) and a coupled configuration (see FIG. 3). In the coupled configuration the through passage 52 is counter-shaped to the tube to be received so as to perfectly couple with it and receives the tube.

The schematic drawings illustrate a situation where the flexible blood tube is coupled to the sensor 50. However, the housing 51 may be alternatively shaped to couple with a rigid cuvette (such as the cuvette for the Hemoscan® sensor of Gambro Lundia). In such a case, the flexible tubing of the blood circuit has the rigid cuvette properly applied so that blood flowing in the extracorporeal blood circuit 60 passes through the cuvette itself; the through passage is in this latter case counter-shaped to the outer surface of the cuvette which is not necessarily rounded, but may alternatively have flat outer surfaces (polygonal section).

It is clear that in case the housing is to be applied to the circular flexible tubing of the extracorporeal blood circuit 60, any position of the sensor along the blood withdrawal line 6 or blood return line 7 is suitable. In case the sensor 50 has a through passage counter-shaped to a specific cuvette, the sensor is to be applied in correspondence of the cuvette itself for proper working.

The housing 51 may be made of a high absorption material which prevents external ambient light from reaching the receivers.

The sensor 50 comprises at least one signal source 53 for directing a signal towards the blood along an emission axis 54.

The signal source 53 may include any suitable signal emitter, such as an optic or an acoustic emitter directing a proper emitted signal towards the inside of the tube where blood is flowing.

In embodiments of the present invention, the signal source 53 includes an electromagnetic radiation source, particularly a light source such as a LED source.

In the following description, we refer to an optical emitter and in detail to a LED emitter 55; however, this should not be interpreted as limiting.

The peak wavelength of the signal source is usually set to 800-810 nm, corresponding to that point of the Hgb absorption spectra where absorption is not dependent on oxygenation. Again, this is not to be considered a limiting aspect.

The specific implementation of the signal source 53 includes a multiple wavelength LED emitter (namely, MTMD6788594SMT6, Marktech Optoelectronics, NY, USA) used for light emission. The emitter 55 in particular includes 5 LEDs on the same chip, with peak wavelengths in the red/infrared bands. The source 53 further comprises a fiber optic 56 having one end 56a coupled with the signal emitter 55 and the other end 56b fixed to the housing 51 and placed to direct the light signal towards the blood along the emission axis 54. As shown in FIG. 3, the second end 56b of the emitter fiber optic 56 is placed at the counter-shaped portion and faces the tube in a coupling condition of the housing with the tube segment 61.

The sensor 50 comprises a plurality of detectors 57 for receiving the signal emitted by said source after at least partially passing through the blood, in particular the detectors 57 collect reflected signal, scattered signal and/or transmitted signal depending on their respective position. Since the emitter 55 is a LED emitter, the detectors 57 include a photodiode receivers 58.

In an advantageous embodiment, the light detectors 57 are placed at different angular degrees with respect to the emission axis 54. In more detail, the sensor 50 of FIG. 3 includes four different detectors 57 for receiving the electromagnetic radiation from the signal source 53, one first photodiode receiver PD1 being placed at about 180° with respect to the emission axis 54 of the signal source, one second photodiode receiver PD2 being placed at about 90° with respect to the emission axis of the signal source, one third photodiode receiver PD3 being placed at about 45° with respect to the emission axis of the signal source, one fourth photodiode receiver PD4 being placed at about 0° with respect to the emission axis of the signal source. Of course, more (or less) than 4 receivers may be used depending on the specific need and more than one receiver may also be placed at the same angular degree with respect to the emission axis 54.

Each detector 57 is configured to receive the signal emitted by the signal source (and duly reflected, scattered or transmitted) radially along the normal section of the blood flow in the tube of the extracorporeal blood treatment apparatus. The new measurement system extends the architecture of the traditional design to collect light at different geometrical angles with respect to the emitter, allowing for discrimination between reflected, scattered and transmitted light. A loss in transmitted light due to an increase in scattering is not falsely detected as an increase in absorbance, if, at the same time, the scattered light is picked up by a different receiver.

In order to achieve the above configuration, each detector 57 includes a respective fiber optic 59, one end being placed in correspondence of the tube segment 61, the other end being coupled to a receiver, in detail a photodiode receiver. In more detail, the end of the fiber optic 59 in correspondence of the tube is fixed to the housing 51 and is placed at the counter-shaped portion and faces the tube in a coupling condition of the housing with the tube segment. As mentioned, all channels for receiving the signals are placed radially along the normal section of the blood flow, except for the reflection channel(0°) which is slightly shifted along the flow direction to allow placement of the emission fibre 56. Both emitted and collected light is coupled to and from the bloodline using e.g. plastic fibre optics (ESKA GH4001, Mitsubishi Rayon).

Photodiode receivers 58 may have a specific fiber-coupling mechanics (e.g. IFD91, Industrial Fiber Optics, Tempe, USA) for light collection channels, corresponding to PD1-4 in FIG. 3.

The photodiode receivers 58 are housed on a printed circuit board 60 along with analog circuitry for transimpedance amplification 62; the circuitry for transimpedance amplification 62 includes a current-to-voltage converter (for example implemented using an operational amplifier). The circuitry 62 can be used to amplify the current output of the photodiode receivers 58. Current-to-voltage converters are used with photodiodes that have a current response that is more linear than the voltage response (it is common for the current response to have better than 1% linearity over a wide range of light input). The transimpedance amplifier presents a low impedance to the photodiode and isolates it from the output voltage of the operational amplifier. There are several different configurations of transimpedance amplifiers, the one factor they all have in common is the requirement to convert the low-level current of a sensor to a voltage.

The printed circuit board 60 further includes lowpass filtering stage 63 and gain-stage amplification. The cutoff frequency of the lowpass filter 63 is set to e.g. 30 Hz. The gain is set to channel-specific values, based on preliminary testing and calibration. The analog signals are then converted into digital signals by a suitable converter 64. In more detail, the analog outputs are sampled at a rate of 100 Hz with 12-bit resolution using an NI USB-6008 DAQ card (National Instruments Italy Srl, Milano, Italy) and recorded by a custom LabView Virtual Instrument.

The multi-LED emitter, the signal conditioning board and the DAQ card were assembled together on a 3D-printed housing and placed inside a grounded metallic box (see FIG. 3) for electro-magnetic shielding, provided with openings for fiber optics 56, 59, data connection and power supply.

The digital signals are input to a controller 65 for being used in detecting one or more parameter of the blood flowing in the tube segment 61 of the extracorporeal blood treatment apparatus, as apparent from the following detailed description.

Modeling and Estimation

The general physical principle for the determination of relevant blood or plasma parameter with non-invasive sensor is linked to the fact that osmolarity alteration changes the shape of red blood cell and so their optical properties change accordingly. Osmolarity is the measure of solute concentration, defined as the number of osmoles of solute per litre of solution. As explained, sodium is the highest concentrated solute in both dialysis fluid and blood plasma and therefore it is the main driver of osmolarity.

The Applicant has therefore understood that a (e.g. light) response signal measured from a (e.g. light) detector in a procedure for blood volume variation estimation is affected by both red cell concentration and osmolarity (and therefore mainly by blood/plasma sodium content).

Moreover, the Applicant also surprisingly uncovered that several detectors placed at different angulations with respect to a tube segment where extracorporeal blood flows have different responses to combined hematocrit (HCT)/blood volume variation ($\Delta$RBV) and osmolarity (OSM)/sodium content ($Na_{pl}$) changes. The basic principle is to use one or more mathematical formulations to de-couple the effect of HCT and $Na_{pl}$ based on data from a generic number N of channels from said N detectors. This approach allows determining a number of blood parameters of interest without the need of sampling blood or affecting the treatment during measurement; the relevant parameters may be selected to be relative blood volume variation ($\Delta$RBV) and plasma sodium concentration according e.g. to the following relationship:

$$\Delta RBV(t) = \text{function}_1(I0(t), I1(t), I2(t), \ldots, I\_N(t));$$

$$Na_{pl}(t) = \text{function}_2(I0(t), I1(t), I2(t), \ldots, I\_N(t)).$$

Wherein I0 identifies the output signal from detector 0; I_N identifies the output signal from detector N. Each detector has its own channel i=1 to N.

There are many possible formulation for said functions. For example, a possible formula is the linear combination of channel values, possibly elevated to a power factor so that each channel affects to a greater or lesser extent the corresponding parameter depending on the effect that the specific blood property has on the signal captured at a specific angular position.

$$\Delta RBV(t) = K0^*(I0(t))^{\hat{}}a0 + K1^*(I1(t))^{\hat{}}a1 +, \ldots, +K\_N^*(I\_N(t))^{\hat{}}aN;$$

$$Na_{pl}(t) = J0^*(I0(t))^{\hat{}}b0 + J1^*(I1(t))^{\hat{}}b1 +, \ldots, +J\_N^*(I\_N(t))^{\hat{}}bN.$$

More complex classificators or neural networks are another possibility. For example, a neural network may be trained so that it receives as input the signals from the various detectors plus (possibly) other input variables linked to blood volume variation and plasma sodium concentration, such as conductivities in the dialysate circuit (both upstream and downstream the filtration unit) and/or sodium concentration in the fresh dialysis fluid. The neural network provides the value of the desired blood parameters as an output, thereby succeeding in decoupling the optical effects of red cell concentration and shape change due to osmolarity.

It is apparent that if the effects of osmolarity can be detected and decoupled, a better estimation of blood volume variation can be obtained. At the same time, it is extremely relevant to note that also an estimation of plasma sodium concentration $Na_{pl}$ can be derived. In other terms, since the sodium content in blood or plasma has the main effect on osmolarity, determining and removing such effects allow a proper estimation of blood volume variation during treatment; additionally, since the effects of plasma sodium concentration are de-coupled, an estimation of such a parameter is also made available. Results shows that some specific channels are mostly sensitive to specific parameters, while the behavior of other channels is more like a mix of properties (hematocrit and osmolarity).

Figure 12:
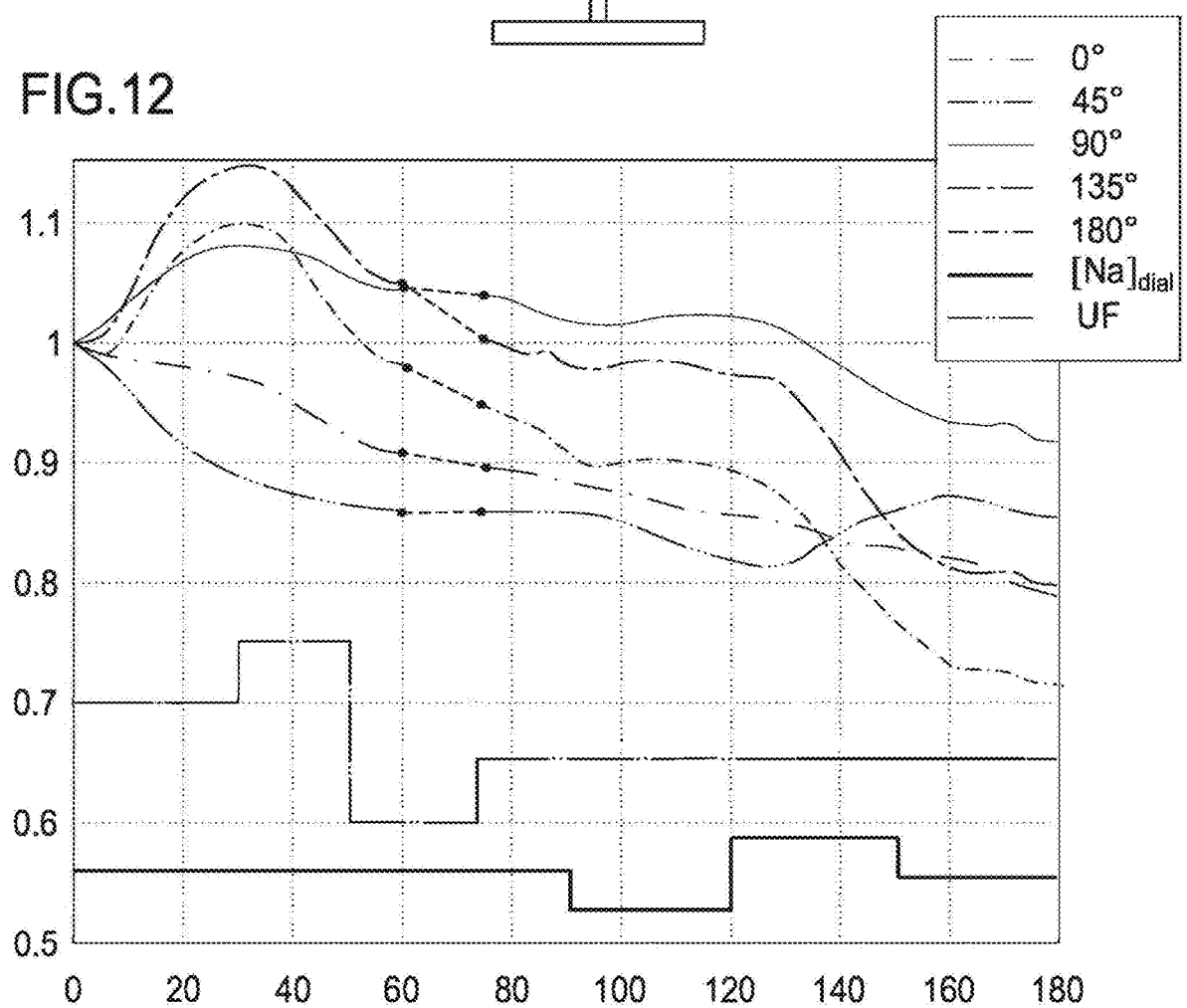
FIG. 12 shows the light intensity measured at a plurality of angular degree, normalized to the value at treatment start.

FIG. 12 shows light intensity measured at different angular degrees, normalized to the value at treatment start. There is a short region in the middle where recording was interrupted to allow for modifications to setup. With respect to the previously described sensor implementation, the graph includes the signal from an additional photodetector placed at 135°; however, the general concept herein explained is not dependent on the number and position of the various detectors.

FIG. 12 shows that the 0° channel (reflected light, red line) is mostly dependent on ultrafiltration and RBV variations.

Figure 13:
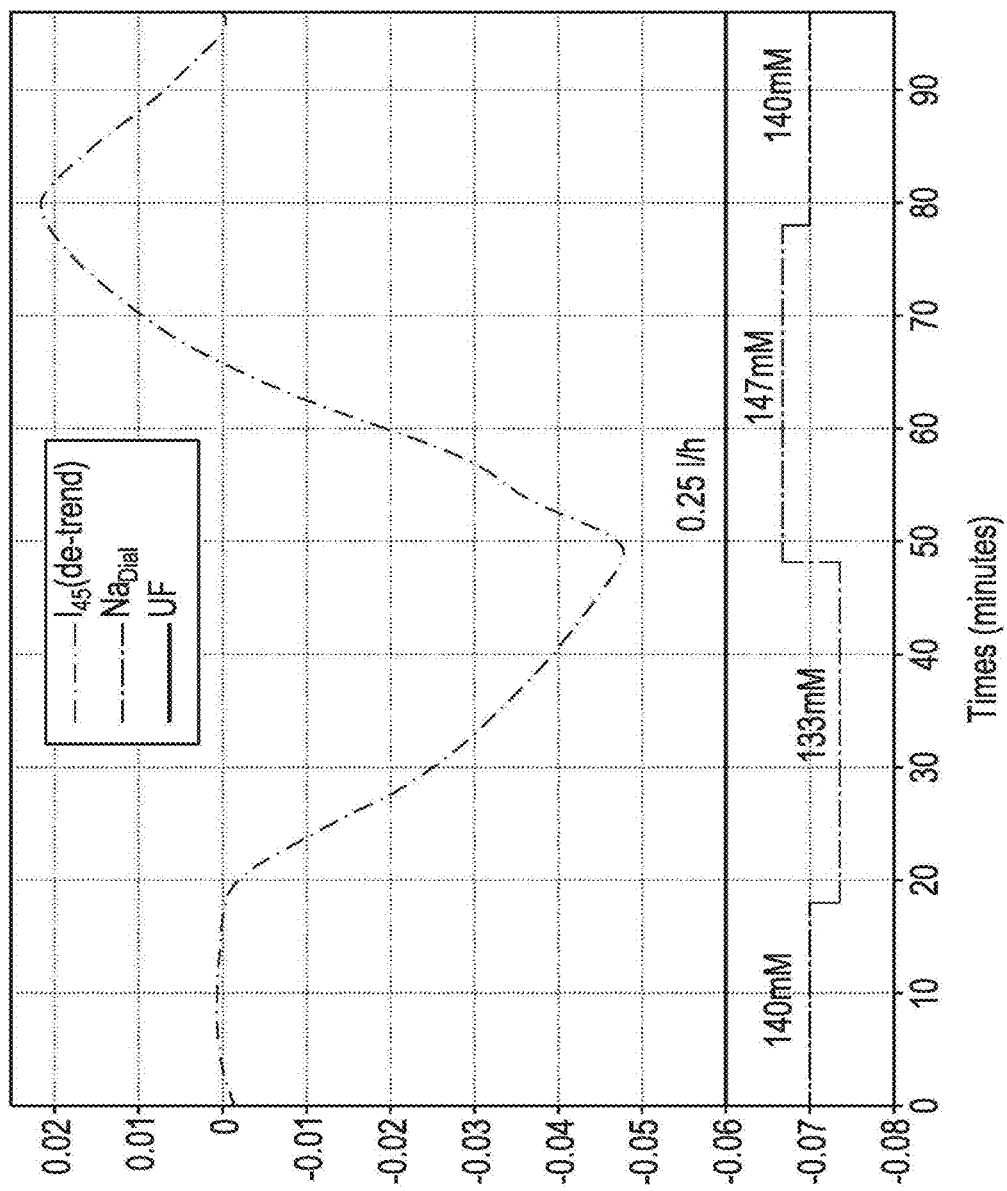
FIG. 13 shows the light intensity measured at the normalized 45° channel; the signal has been subjected to a de-trend procedure to remove slow drift due to the RBV effect.

FIG. 13 shows the normalized 45° channel (scattered light, blue line). This signal has been subjected to a de-trend procedure to remove slow drift due to the RBV effect. This procedure was not applied with a real-time algorithm, but the linear combination approach may be used to create a real-time de-trend. As shown in figure, the de-trended 45° channel is able to detect osmolarity variations caused by dialysate sodium concentration changes. The first-order response is mainly due to the time needed for blood sodium concentration to adjust to the dialysate sodium value.

In other terms, the various signals detected at different angular locations are differently affected by plasma sodium and relative blood volume changes. Therefore, with proper signal manipulation it is possible to more precisely determine the two mentioned blood parameters in real time and non-invasively.

A possible approach to build equations that allows to determine the mentioned blood parameters, namely blood volume variation $\Delta$RBV and plasma sodium concentration $Na_{pl}$, or parameters which are strictly related to $\Delta$RBV and $Na_{pl}$, such as hemoglobin concentration or plasma conductivity, starts from the one-compartment model of the blood as shown in FIG. 7. The following equations are used to define the modeling (the terms in the following equations are defined in the Glossary section):

$$V_B(t) = V_{B,0} + \int_0^t (-J_{UF}(\tau) + J_{Ref}(\tau)) d\tau \qquad (1)$$

$$\Delta RBV(t) = \frac{V_B(t) - V_{B,0}}{V_{B,0}} = \frac{\int_0^t (-J_{UF}(\tau) + J_{Ref}(\tau)) d\tau}{V_{B,0}} \qquad (2)$$

$$\Delta \dot{RBV}(t) = \frac{-J_{UF}(t) + J_{Ref}(t)}{V_{B,0}} \qquad (3)$$

$$Na_{Pl}(t) = \frac{K_{DIFF} \cdot (Na_{In}(t) - Na_{Pl}(t)) + J_{REF}(t) \cdot (Na_{Ref}(t) - Na_{Pl}(t))}{V_B(t)} \quad (4)$$

The Glossary provides the variable definitions.

Equation (1) defines the relationship between absolute blood volume $V_B(t)$ and flow rates.

Equation (2) defines relative blood volume $\Delta RBV(t)$ on the basis of absolute blood volume $V_B(t)$. Equation (3) describes $\Delta RBV(t)$ in differential form. $J_{UF}(t)$ is known and may be provided to the controller 65 of the sensor 50 by the extracorporeal blood treatment apparatus 1 (namely by the control unit 10).

$Na_{Pl}(t)$ is computed according to equation (4), where $Na_{in}(t)$ and $J_{REF}(t)$ are experimentally determined, $V_B(t)$ is computed from equation (2) and $K_{Diff}$, the membrane diffusion coefficient for sodium, may be set to the typical value of 250 ml/min or set based on the used membrane. Computation of $Na_{Pl}(t)$ requires an initial value. Preliminary attempts to compute $Na_{Pl}(t)$ revealed the presence of a session-specific offset associated with inter-session events, like instrument recalibration and sodium electrode replacement. Therefore, a baseline adjustment was applied when computing $Na_{Pl}(t)$ to account for this offset.

State-Space Modeling and Estimation

A state-space approach was chosen for estimation of $\Delta RBV(t)$ and $Na_{Pl}(t)$, treated as state variables that completely describe the system under observation. A set of modeling equations describe the evolution of the state variables and the input/output relationship. The estimation was accomplished using a Kalman filtering technique applied to the modelling equations as apparent from the following description. Classification of sensor data as being either input or output depends on whether the specific variable monitored by each sensor perturbs the system state or is determined by it. The inlet dialysate sodium concentration $Na_{In}(t)$ and the inlet dialysis fluid conductivity $\sigma_{In}(t)$ constitute the input variables; these variables are known since the operator usually sets either the inlet dialysis fluid conductivity $\sigma_{In}(t)$ or the electrolyte (e.g. sodium) concentration; once one variable is set the other is automatically determined. Moreover, one or both the inlet dialysis fluid conductivity $\sigma_{In}(t)$ and the inlet dialysate sodium concentration $Na_{In}(t)$ may be measured. For example, the second probe 109 of FIGS. 1 and 2 may be a conductivity meter and thereby measure the inlet dialysis fluid conductivity $\sigma_{In}(t)$ along time.

The hemodialysis machine maintains the effective value of $Na_{In}(t)$ within clinically acceptable boundaries of the value set by the operator. Due to the general properties of electrolyte solutions, and the fact that sodium is the most concentrated electrolyte in plasma and dialysate, a good correlation can be found between the two fluids' electrical conductivity and sodium concentration. The output sensor data consists of the (optical) outputs $\Delta RP_1(t)$ to $\Delta RP_4(t)$ and the outlet conductivity $\sigma_{Out}(t)$. Notably, the outlet conductivity $\sigma_{Out}(t)$ may be measured by the extracorporeal blood treatment apparatus using the auxiliary conductivity meter 112 placed in the spent dialysis fluid line 13.

$$\Delta RP_i(t) = \frac{V_{Out,i}(t) - V_{Out,i}(0)}{V_{Out,i}(0)} \quad i = 1, 2, 3, 4 \quad (5)$$

$$\Delta \dot{RBV}(t) = 0 \quad (6)$$

$$Na_{Pl}(t) = \frac{Na_{In}(t) - Na_{Pl}(t)}{\tau_{Diff}} \quad (7)$$

The ordinary differential equations (6) and (7) model the blood pool dynamics, and were developed by removing the terms with parameters unknown during clinical practice ($V_{B,0}$, $J_{Ref}$, $Na_{Ref}$) from equations (3) and (4). One critical part of the estimation procedure is the handling of non-modeled terms: thanks to the properties of the Kalman filter, the lack of some terms, vice versa included in equations (3)-(4) and not included in equations (6)-(7), can be accounted for as noise in process modeling. This way, although refilling properties and starting blood volume are not known exactly, their influence on the reliability of the estimation is taken into account.

While equation (3) would be a better theoretical description, $V_{B,0}$ and $J_{Ref}(t)$ are not known in clinical routine. By employing the approximate version according to equation (6), no time-dependent evolution of $\Delta RBV$ is predicted, but the Kalman filter technique includes a measurement-based correction step which is applied to the model prediction. This correction is applied to the static $\Delta RBV$ value at each time step, thus making $\Delta RBV$ a quasi-static variable.

Equation (7) approximates equation (4): the parameters of the refilling process are not clinically available during treatment, so only sodium diffusion is modeled by employing a diffusion time constant $\tau_{Diff}$ to describe how plasmatic sodium is related to $Na_{In}(t)$. $\tau_{Diff}$ can be viewed as an estimate of $V_B(t)/K_{Diff}$ from equation (5). For $K_{Diff}=250$ ml/min (realistic value for sodium) and $V_B=51$ (a time-independent average value), we have that $\tau_{Diff} \cong 1200$ s. By fitting a first-order step response of outlet conductivity $\sigma_{Out}(t)$ to experimental data, an estimate of $\tau_{Diff} \cong 1000$ s was obtained. Therefore, an intermediate value of $\tau_{Diff} \cong \cong 1100$ s may be used in the filter model.

$$\Delta RP_i(t) = G_{Opt,i,1} \cdot \Delta RBV(t) + G_{Opt,i,2} \cdot Na_{Pl}(t) + G_{Opt,i,3} \quad (8)$$

$$\begin{bmatrix} \Delta RP_1(t) \\ \Delta RP_2(t) \\ \Delta RP_3(t) \\ \Delta RP_4(t) \end{bmatrix} = G_{Opt} \cdot \begin{bmatrix} \Delta RBV(t) \\ Na_{Pl}(t) \\ 1 \end{bmatrix} \quad (9)$$

A linear formulation may be chosen for $\Delta RP_i(t)$ which is described in equation (8), where i=1, ...,4 indicates the output channel of the receiver. The [4×3] matrix $G_{opt}$ in (9) contains weighting coefficients for all channels of signal detectors, estimated by multivariate regression analysis.

$$\sigma_{Out}(t) = \sigma_{in} \cdot \left(1 - \frac{D}{J_D}\right) + \sigma_{pl} \cdot \frac{D}{J_D} \quad (10)$$

$$\sigma_{Out}(t) = G_{Mix} \cdot \sigma_{Pl}(t) + (1 - G_{Mix}) \cdot \sigma_{In}(t - \tau_{Delay}) \quad (11)$$

$$\sigma_{Pl}(t) = G_{Na,Gain} Na_{Pl}(t) + G_{Na,offset} \quad (12)$$

The last output element, i.e., the outlet dialysate conductivity $\sigma_{Out}(t)$, is modeled as a weighted average of the inlet and plasmatic conductivities. In equation (10), $\sigma_{Out}$ is a weighted average based on the dialysance D and the dialysis flow rate $J_D$. A simpler formulation is in equation (11) deriving from the previous equation, where $G_{Mix}=D/J_D$. As an approximation, $J_D$ may be fixed to 500 ml/min and given an average value of D=250 ml/min, a value of 0.5 for the mixing constant $G_{mix}$ may be imposed. A delay term $\tau_{delay}$ was included, to account for the propagation time of changes in the inlet dialysate composition across the hydraulic circuit. A value of $\tau_{delay}$=140s was estimated by measuring the step response delay of $\sigma_{Out}(t)$ in the sessions where sodium concentration steps were applied.

The plasmatic conductivity $\sigma_{Pl}(t)$ is modeled in equation (12) as a linear function of plasmatic sodium concentration $Na_{Pl}(t)$. The coefficients $G_{Na,Gain}$ and $G_{Na,Offset}$ were estimated by linear regression starting from experimental data.

Figure 6:
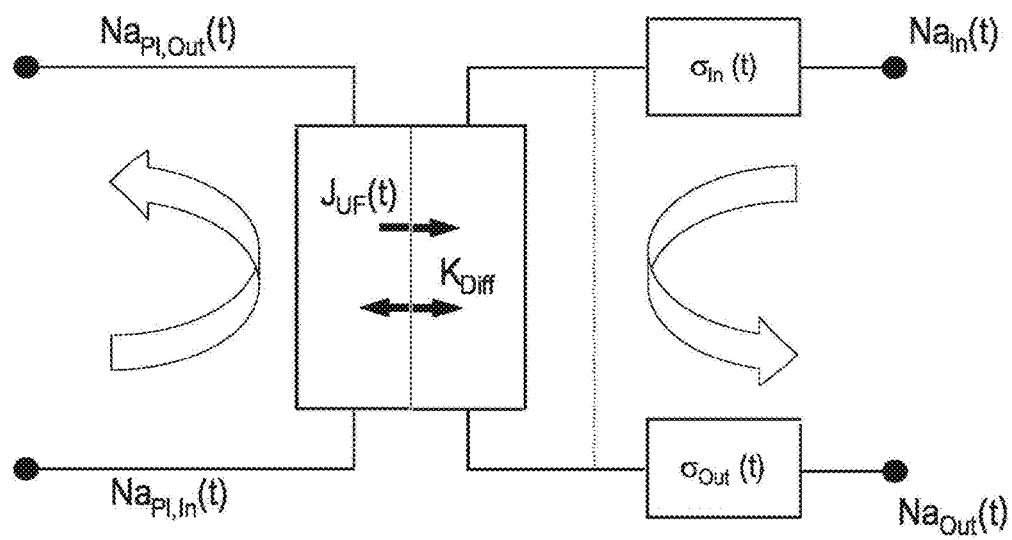
FIG. 6 is a diagram of the hemodialyzer with inlet/outlet ports for blood and dialysate, wherein conductivity cells measure the inlet ($\sigma_{In}$) and outlet ($\sigma_{Out}$) dialysate electrical conductivity; the dotted black line representing a bypass condition.

FIG. 8 illustrates the relationship between input signals, state variables and output signals. The hemodialysis machine periodically goes into bypass mode, either for safety reasons or for the purpose of internal recalibration. During bypass, ultrafiltration is suspended and the hydraulic connection of dialysate to the hemodialyzer is short-circuited, see FIG. 6 (dotted line), meaning that data from the conductivity cells ($\sigma_{In}(t)$, $\sigma_{Out}(t)$) is not useful during by-pass condition since the inlet fresh dialysis fluid is directly routed towards the effluent line without entering the filtration unit. In view of the bypass condition, certain changes in the modeling equations are needed to reflect such temporary alterations of the physical system. During bypass, the temporary stop in ultrafiltration implies that $J_{UF}(t)$=0, and, given the lack of information about $J_{Ref}(t)$ during clinical practice, equation (6) is still the best available approximation for ΔRBV modeling. For this reason, equation (6) is kept and not replaced. The hydraulic disconnection of the filtration unit, e.g. the hemodialyzer, during bypass implies that diffusion is suspended, here modeled by replacing equation (7) with the following equation (13):

$$\dot{Na}_{Pl}(t)=0 \tag{13}$$

This temporary replacement is also reflected by modifications to the process noise for $Na_{Pl}(t)$. During bypass, data coming from the conductivity cells is not useful due to the different hydraulic path of the dialysate, which is not routed into the fluid chamber of the filtration unit. This is reflected by setting the sensitivity of the filter related to $\sigma_{In}(t)$ and $\sigma_{Out}(t)$ to zero during bypass. FIG. 9 depicts the transition model regulating switching of the Kalman filter between standard mode, bypass mode and build-up mode. During build-up mode, the alterations of the filter structure associated with the bypass conditions are maintained for an additional period of time $\tau_{Delay}$, to allow the accumulation of the necessary delay of $\sigma_{In}(t)$ before returning to default filter operations.

Kalman filtering is basically an algorithm that uses a series of measurements observed over time, containing statistical noise and other inaccuracies (e.g. due to equation simplifications), and produces estimates of unknown variables that tend to be more accurate than those based on a single measurement alone, by estimating a joint probability distribution over the variables for each timeframe. The algorithm works in a two-step process. In the prediction step, the Kalman filter produces estimates of the current state variables, along with their uncertainties. Once the outcome of the next measurement (necessarily corrupted with some amount of error, including random noise) is observed, these estimates are updated using a weighted average, with more weight being given to estimates with higher certainty. The algorithm is recursive and may run in real time, using only the present input measurements and the previously calculated state and its uncertainty matrix; no additional information is required.

The following equations (14) to (18) define an example of the Kalman filter which might be employed according to present embodiments.

$$x_k^- = f(x_{k-1}^+, u_k) \tag{14}$$

$$P_k^- = A \cdot P_{k-1}^+ \cdot A^T + Q \tag{15}$$

$$E_k = P_k^- \cdot H^T \cdot (H \cdot P_k^- \cdot H^T + R)^{-1} \tag{16}$$

$$x_k^+ = x_k^- + E_k \cdot (z_k - g(x_k^-, u_k)) \tag{17}$$

$$P_k^+ = (I - E_k \cdot H) \cdot P_k^- \tag{18}$$

These above equations are given as a function of the generic time step k. A time step of is may be for example chosen. Equations (14) and (15) represent the prediction step, where modeling knowledge of the system is employed, and equations 16 to 18 represent the measurement-based correction step.

The input $u_k$ is a [2×1] vector which includes $Na_{In}[k]$ and $\sigma_{In}[k]$. The vectors $x_k^-$ and $x_k^+$ (both [2×1]) contain the predicted and corrected values of the state variables ΔRBV[k] and $Na_{Pl}[k]$. $x_k^-$ is the predicted system state at step k, and is a function f(•,•) of $x_{k-1}^+$ and $u_k$. The elements of initial vector $x_0^+$ may be set to ΔRBV=0 and $Na_{Pl}$=140 mM. In other terms, the initial vector includes a null blood volume variation and a subject average plasma sodium concentration.

Function f(•,•) is defined by the discretized versions of equations (6) and (7) in standard mode, and by the discretized equations (6) and (13) in bypass mode. Discretization of equations (6), (7) and (13) is respectively implemented with the forward Euler method; the discretized equations are:

$$\Delta RBV[k] = \Delta RBV[k-1] \tag{19}$$

$$Na_{Pl}[k] = Na_{Pl}[k-1] \cdot \left(1 - \frac{1}{\tau_{Diff}}\right) + \frac{1}{\tau_{Diff}} \cdot Na_{In}[k] \tag{20}$$

$$Na_{Pl}[k] = Na_{Pl}[k-1] \tag{21}$$

respectively. Equation 21 being used instead of equation 20 during the by-pass condition. The [2×2] matrix Q describes the process noise covariance. The matrix A is the [2×2] Jacobian linearization of f(•,•) with respect to ΔRBV and $Na_{Pl}$.

A standard $Q_{std}$ matrix is used during standard filter operation, replaced by $Q_{bypass}$ during bypass mode. Both versions of Q are diagonal matrices whose elements are precomputed, on the basis of realistic maximum values for the non-modeled terms of the process equations. The error gain $E_k$ is a [2×5] matrix computed according to equation (16).

The measurement noise is characterized by the [5×5] covariance matrix R, taken to be a pre-determined diagonal matrix. The diagonal values of R, associated with optical measurements, were set equal to the root-mean-square fitting residuals of equation (9). The diagonal value of R associated with $\sigma_{Out}$ modeling was chosen on the basis of realistic deviations of D from the average value considered for equation (11).

The observation vector $Z_k$ is a [5×1] column vector of experimentally measured system output, composed of the optical output $\Delta RP_1[k]$ to $\Delta RP_4[k]$ and outlet conductivity $\sigma_{Out}[k]$. $g(x_k^-, u_k)$ is a [5×1] column vector of predicted output calculated according to state-output function g(•,•).

The function $g(\bullet,\bullet)$ is determined by the time-discrete versions of equations (9) and (11), given by $$\begin{bmatrix} \Delta RP_1(k) \\ \Delta RP_2(k) \\ \Delta RP_3(k) \\ \Delta RP_4(k) \end{bmatrix} = G_{Opt} \cdot \begin{bmatrix} \Delta RBV(k) \\ Na_{Pl}(k) \\ 1 \end{bmatrix} \quad (22)$$

$$\sigma_{Out}[k] = G_{Mix} \cdot \sigma_{Pl}[k] + (1 - G_{Mix}) \cdot \sigma_{In}[k - k_{Delay}] \quad (23)$$

respectively. In equation (23), $k_{Delay}$ is the discrete version of $\tau_{Delay}$ and $\sigma_{Pl}[k]$ is computed according to $$\sigma_{Pl}[k] = G_{Na,Gain} \cdot Na_{Pl}[k] G_{Na,Offset} \quad (24)$$

which is the discretized version of equation (12).

The matrix H from equations (16) and (18) is the [5×2] Jacobian linearization of $g(\bullet,\bullet)$ in respect to $\Delta RBV$ and $Na_{Pl}$. Two versions of H exist: $H_{std}$ and $H_{bypass}$. During default machine operations $H_{std}$ is used. During bypass, $H_{std}$ is replaced with $H_{bypass}$ to ensure that the measurement-based correction step is insensitive to $\sigma_{In}[k]$ and $\sigma_{Out}[k]$. The matrices $P_k^-$ and $P_k^+$ are the predicted and corrected [2×2] estimation covariances, respectively. Both matrices are computed at each step k, according to equations (15) and (18), initiated by a diagonal matrix $P^+$ with the initial uncertainties of $\Delta RBV$ and $Na_{Pl}$ set to 0 and 4 mM, respectively. Zero uncertainty on starting $\Delta RBV$ is given by the fact that $\Delta RBV$ is a relative variation and its starting value is always known and equal to 0. The initial uncertainty for $Na_{Pl}$ is based on the assumption of a 136-144 mM physiological range for patients at treatment start.

Computation of $P^+$ is an important feature of the Kalman filter, given that it represents covariance of the state variables. As described in equations (15) and (18), the estimation covariance is influenced by the covariance of the modeling and measurement processes. On this basis, P is a useful additional source of information about the uncertainty of the estimation: we choose to use the square root of the diagonal elements $P_{11}$ and $P_{22}$ from $P^+$ in equation (18) as an indicator of uncertainty, resulting in confidence intervals of $\Delta RBV \pm \sqrt{P_{11}}$ and $Na_{Pl} \pm \sqrt{P_{22}}$.

The use of the simplified blood pool model equations and of the Kalman filter approach allows to determine and monitor the state variables along time, namely relative blood volume variation $\Delta RBV$ and plasma sodium concentration $Na_{pl}$ are known to the system and updated at each time stamp k. Knowledge of the blood parameters substantially in real time allows the extracorporeal blood treatment machine to determine other relevant treatment aspects, such as filter efficiency and/or to more precisely follow proper profiling of patient values.

In accordance with the above described aspects, the controller 65 is configured for calculating the concentration of sodium present in the fluid flowing through said segment 61 of the extracorporeal blood circuit 60 based the output signal received by the detectors 57. For instance if the segment is part of the blood withdrawal line and the fluid is blood, the controller 65 may continuously determine the concentration of sodium present in the blood flowing through the blood withdrawal line, while if the segment is part of the blood return line and the fluid is blood, the control unit or the detection circuit may continuously calculate the concentration of sodium present in the blood flowing through the blood return line. $Na_{pl}$ of blood circulating in the extracorporeal circuit may be calculated and blood volume variation (independent form osmolarity) may be determined, e.g. by the controller 65.

Furthermore the controller 65 (or correspondingly the apparatus control unit 10) may be configured to determine at least one value of a parameter (D, K·t) indicative of the effectiveness of the extracorporeal blood treatment based on the measure of plasma sodium concentration of the blood circulating in the tube segment (e.g., based on the determination of plasma sodium concentration during an extracorporeal blood treatment).

In detail, the controller 65 may be configured for commanding execution of the following steps:
causing flow of a patient's blood in the extracorporeal blood circuit 60 at a blood flow rate Qb, e.g. acting on the blood pump 11 once the extracorporeal circuit has been properly mounted on the respective holder(s) and connected to the patient;
causing a fresh treatment liquid to flow in the preparation line 19 towards the secondary chamber 4 at a flow rate $(Qd_{in})$; for example this may be achieved operating pump 21, and in the case the apparatus comprises preparation section 100 also properly coordinating pumps 105 and 108;
causing a used treatment liquid to flow in the spent dialysate line 13 at a flow rate $Qd_{out}$; this may be achieved operation pump 17 and optionally pump 27;
receiving one or more values related to the conductivity $(\sigma_{in})$ or to the concentration of a substance $(Na_{in})$ of the fresh treatment liquid flowing in the preparation line 19; the substance may be one single element such as one electrolyte or a group of elements such as a set of electrolytes: for instance sensor 109 may provide the control unit 10 with an information relating to conductivity or to concentration of a given, e.g. sodium, substance; or the set values for conductivity or concentration of the substance may be used;
receiving one or more measured values related to the conductivity $(\sigma_{out})$ or to the concentration of said substance $(Na_{out})$ in the used treatment liquid flowing in the spent dialysate line 13; a sensor 112 capable of detecting conductivity or concentration; for instance a conventional concentration or conductivity sensor ay provide the control unit 10 with an information relating to conductivity or to concentration of a given substance;
computing at least one value of a parameter D, K·t indicative of the effectiveness of the extracorporeal blood treatment based on:
said one or more measured values related to the conductivity $(\sigma_{out})$ or to the concentration of said substance $(Na_{out})$ of the used treatment liquid;
said one or more set or measured values of the conductivity $(\sigma_{in})$ or to the concentration of said substance $(Na_{in})$ of the fresh treatment liquid;
said calculated value of the plasmatic conductivity $\sigma_{pl}$ or of the plasma sodium concentration $Na_{pl}$ of said substance in blood flowing through said segment 61 of the extracorporeal blood circuit 60;
at least one of: said flow rate $Qd_{in}$ of fresh treatment liquid and said flow rate $Qd_{out}$ of used treatment liquid.

Alternatively, the apparatus may comprise at least two of the described electric parameter sensors 50: each one of these two sensors 50 would have the features of sensor 50 described above with a first tubular segment 61 of the blood withdrawal line received in the housing body of a first of said two sensors 50 and a second tubular segment 61 of the blood return line received in the housing body of a second of said two sensors 50. In this alternative, the controller 65 (connected to each blood/plasma parameter sensor 50) may be configured for:
- causing flow of a patient's blood in the extracorporeal blood circuit at a blood flow rate Qb, e.g. acting on the blood pump 11 once the extracorporeal circuit has been properly mounted on the respective holder(s) and connected to the patient;
- causing a fresh treatment liquid to flow in the preparation line 19 towards the secondary chamber 4 at a flow rate $Qd_{in}$; for example this may be achieved operating pump 21, and in the case the apparatus comprises preparation section 100 also properly coordinating pumps 105 and 108;
- causing a used treatment liquid to flow in the spent dialysate line 13 at a flow rate $Qd_{out}$; this may be achieved operation pump 17 and optionally pump 27;
- receiving one or more values related to the conductivity ($\sigma_{in}$) or to the concentration of a substance ($Na_{in}$) of the fresh treatment liquid flowing in the preparation line 19; the substance may be one single element such as one electrolyte or a group of elements such as a set of electrolytes: for instance sensor 109 may provide the control unit 10 with an information relating to conductivity or to concentration of a given substance; or the set values for conductivity or concentration of the substance may be used;
- receiving or calculating a value of conductivity ($\sigma_{pl,in}$) or of the concentration ($Na_{pl,in}$) of said substance in the blood flowing inside said first segment (61) and a value of the conductivity ($\sigma_{pl,out}$) or of the concentration ($Na_{pl,out}$) of said substance in the blood flowing inside said second segment 61, using the two sensors 50 installed on the blood withdrawal and return lines as just described;
- computing at least one value of a parameter D, K·t indicative of the effectiveness of the extracorporeal blood treatment based on:
  - said one or more values of the conductivity ($\sigma_{in}$) or to the concentration of said substance ($Na_{in}$) of the fresh treatment liquid;
  - said value of conductivity ($\sigma_{pl,in}$) or of the concentration ($Na_{pl,in}$) of said substance in the blood flowing inside said first segment (61) and said value of conductivity ($\sigma_{pl,out}$) or of the concentration ($Na_{pl,out}$) of said substance in the blood flowing inside said second segment,
  - said blood flow rate $Q_b$.

Note that given the knowledge of the plasma sodium concentration $Na_{pl}$ the conductivity of the fluid (blood) in the extracorporeal blood circuit may be determined; the step of causing a fresh treatment liquid to flow in the preparation line 19 comprises the sub-step of maintaining, at least for a time interval T during which the measurements of conductivity or concentration take place, the concentration of the substance ($Na_{in}$) or the conductivity ($\sigma_{in}$) in the fresh treatment liquid constant at a set value which is used for computing the at least one value of a parameter D, K·t indicative of the effectiveness of the extracorporeal blood treatment. At least during said time interval T the control unit 10 is configured to keep constant the flow rate $Qd_{in}$ of fresh treatment liquid in the preparation line 19, the flow rate $Q_b$ of patient's blood in the extracorporeal blood circuit, and the flow rate $Q_F$ of ultrafiltration flow through the semipermeable membrane.

In practice there is no need to alter the conductivity in order to arrive at the determination of dialysance or dialysis dose.

Going in further detail the parameter indicative of the effectiveness of the extracorporeal blood treatment is dialysance D for said substance which is calculated using one of the following formulas:

$$D = \frac{Qd_{in} \times (\sigma_{in} - \sigma_{out}) + Q_F \times \sigma_{out}}{\sigma_{in} - \sigma_{pl}}$$

or $$D = \frac{Qd_{in} \times (Na_{in} - Na_{out}) + Q_F \times Na_{out}}{Na_{in} - Na_{pl}}$$

or $$D = \frac{Qb_{in} \times (\sigma_{pl,in} - \sigma_{pl,out}) + Q_F \times \sigma_{pl,out}}{\sigma_{pl,in} - \sigma_{in}}$$

$$D = \frac{Qb_{in} \times (Na_{pl,in} - Na_{pl,out}) + Q_F \times Na_{pl,out}}{Na_{pl,in} - Na_{in}}$$

wherein

| | |
|---|---|
| D | Treatment unit dialysance |
| $Qd_{in}$ | Fresh dialysis fluid flow rate at the treatment unit inlet |
| $Q_F$ | Ultrafiltration flow rate |
| $\sigma_{in}$ | Inlet dialysate conductivity at the inlet of the filtration unit |
| $\sigma_{Out}$ | Outlet dialysate conductivity at the outlet of the filtration unit |
| $\sigma_{pl}$ | Plasmatic conductivity |
| $Na_{In}$ | Inlet dialysate sodium concentration at the inlet of the filtration unit |
| $Na_{out}$ | Outlet dialysate sodium concentration at the outlet of the filtration unit |
| $Na_{Pl}$ | Plasma sodium concentration in tube segment |
| $\sigma_{pl,in}$ | Plasmatic conductivity at the inlet of the filtration unit |
| $\sigma_{pl, out}$ | Plasmatic conductivity at the outlet of the filtration unit |
| $Na_{Pl, in}$ | Plasma sodium concentration in tube segment upstream the filtration unit |
| $Na_{Pl, out}$ | Plasma sodium concentration in tube segment downstream the filtration unit |

Once dialysance has been calculated then the instant values of dialysance may be integrated over time in order to arrive at the determination of the K·t value in a manner which is per se known and not herein further described.

Figure 14:
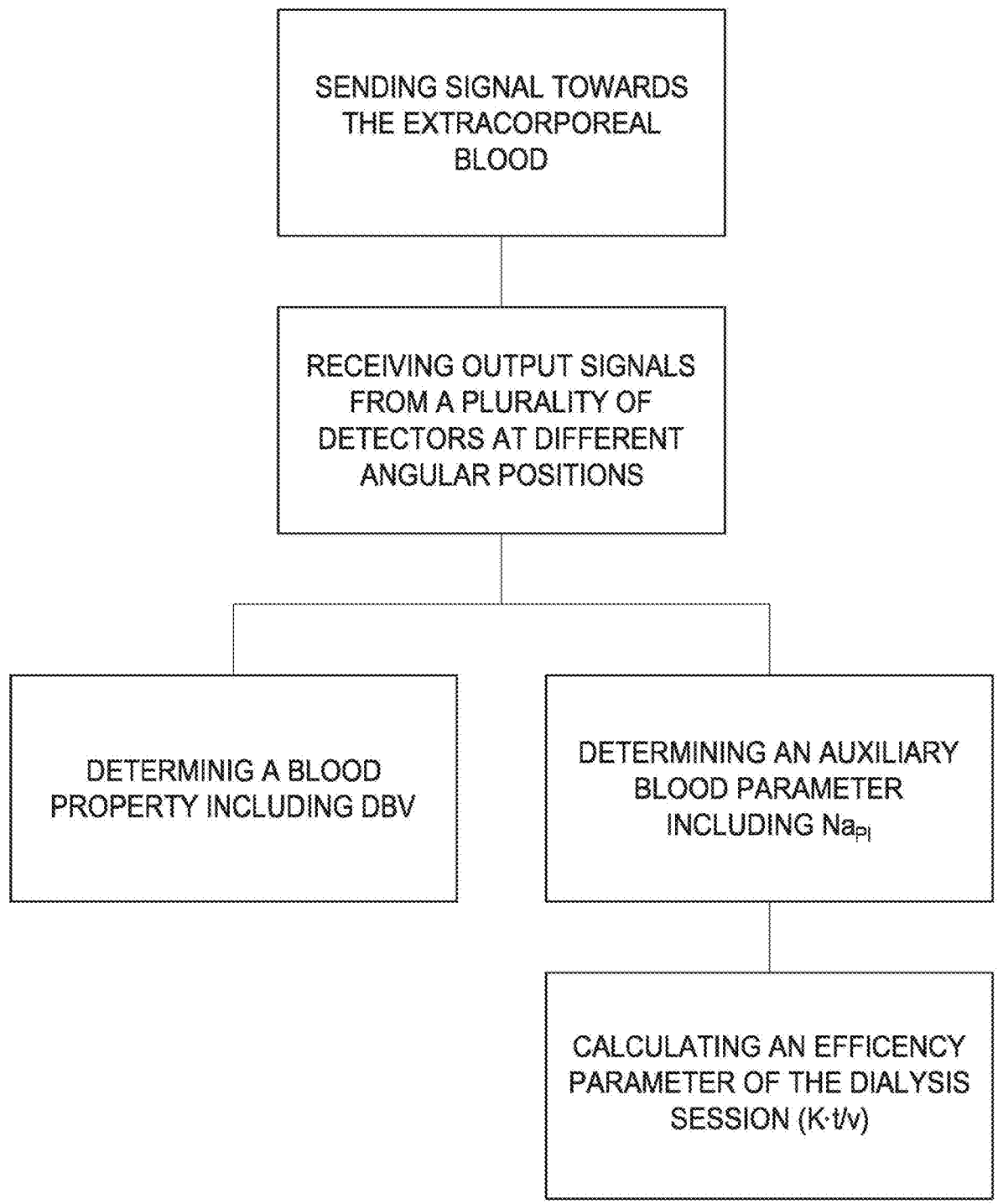
FIG. 14 is a flow chart illustrating the main steps of the process for determining the property and the auxiliary parameter of the extracorporeal blood.

The invention also relates to a process of determining the blood or plasma parameters using the sensor 50 and/or the apparatus for extracorporeal treatment of blood as disclosed above or as claimed in any one of the appended claims. FIG. 14 shows the main steps of the process including sending a signal towards the extracorporeal blood and receiving the reflected, transmitted and/or scattered signal by means of the receivers placed at different angular positions around the tube segment. The process includes determining (as above illustrated) the blood property (e.g. blood volume variation ΔBV) and/or the auxiliary blood parameter (e.g. $Na_{pl}$). The flow process for determining the blood property and the auxiliary blood parameter is illustrated in FIG. 8 wherein the relationship between input signals, state variables and output signals are shown; the dotted lines represents connections which are unreliable during bypass mode. The aspects provide additional details in respect to process implementation.

Control Unit

As already indicated the apparatus according to the invention makes use of a control unit 10 and the sensor of at least one controller 65. Notably, the controller 65 of the sensor 50 may be part (software and/or hardware part) of the control unit 10 of the extracorporeal blood treatment apparatus or may be a separate processing unit. Both control unit 10 and controller 65 may comprise a digital processor (CPU) with memory (or memories), an analogical type circuit, or a combination of one or more digital processing units with one or more analogical processing circuits. In the present description and in the claims it is indicated that the control unit/controller is "configured" or "programmed" to execute certain steps: this may be achieved in practice by any means which allow configuring or programming the control unit/controller. For instance, in case of a control unit/controller comprising one or more CPUs, one or more programs are stored in an appropriate memory: the program or programs containing instructions which, when executed by the control unit/controller, cause the control unit to execute the steps described and/or claimed in connection with the control unit/controller. Alternatively, if the control unit/controller is of an analogical type, then the circuitry of the control unit/controller is designed to include circuitry configured, in use, to process electric signals such as to execute the control unit/controller steps herein disclosed.

Experimental Sessions

An experimental protocol for in-vitro hemodialysis sessions with perturbations of ΔRBV and/or $Na_{Pl}$ was designed to gather robust and representative data for the development and validation of the above proposed and described estimation apparatus and method.

12 lin-vitro hemodialysis sessions were carried out using fresh heparinized bovine blood and an Artis® hemodialysis machine (Baxter, Medolla, Italy). Before each session, hematocrit was measured with the capillary centrifugation method and the blood was diluted with saline solution to achieve 30% hematocrit. For each session, the starting volume of the blood was $V_{B,0}$=5l. The blood flow rate $J_B$ and dialysate flow rate $J_D$ were set to typical clinical values, i.e. $J_B$=300 ml/min and $J_D$=500 ml/min.

Figure 4:
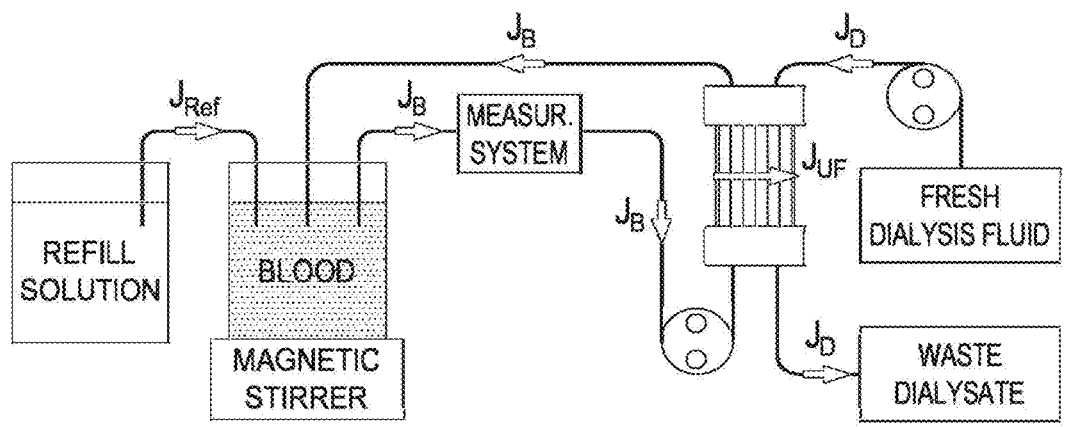
FIG. 4 is a diagram of an experimental setup.

During clinical hemodialysis, water removal from the patient's blood pool is partially compensated by refilling—a phenomenon in which liquid shifts from other body compartments to the circulatory system to maintain physiological blood pressure. Refilling is simulated in the sessions by using a peristaltic pump and a container of fresh dialysis fluid, with a chemical composition similar to plasma; see FIG. 4 for a schematic diagram of the setup.

Relative blood volume loss was implemented by setting the ultrafiltration rate to $J_{UF}$=0.8 L/h and the refilling rate to $J_{Ref}$=0.63 L/h. The difference between these flows allowed to reach a physiological end-session ΔRBV of ≅10%.

Figure 5:
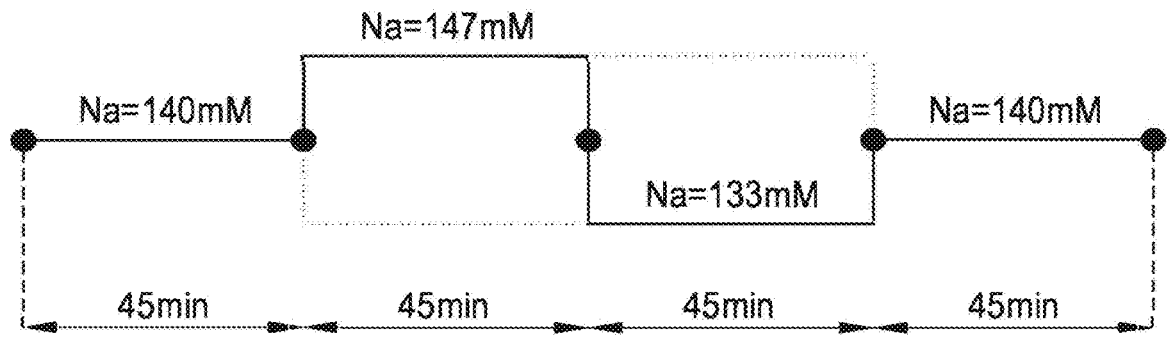
FIG. 5 is the sodium step protocol for the inlet dialysis fluid $Na_{In}$ upstream the filtration unit; the dotted line showing the dual protocol with inverted steps and the large black dots indicating the times for blood gas sampling.

Changes in plasma sodium concentration $Na_{Pl}$ were implemented by applying steps to the inlet dialysate sodium concentration Nam. Changes in Nam propagate to $Na_{Pl}$ by diffusion across the membrane of the hemodialyzer in a manner that can be approximated as a first-order response. The concentration was initially set to 140 mM, and then two steps of ±7 mM (with respect to the 140 mM baseline) were applied before returning to 140 mM. Each concentration value was maintained for 45 min. The order of the positive and negative steps is changed between sessions. The protocol is illustrated in FIG. 5. Each session was composed of a 1-h adjustment phase followed by a 3-h experimental phase. The adjustment phase was designed to achieve equilibrium between dialysate and blood to improve reproducibility of the experimental sessions, since each fresh volume of bovine blood may come with different plasmatic concentrations of electrolytes. During the adjustment phase $Na_{In}$ is maintained constant. In this way, the blood reaches standard initial conditions before the start of the actual experiment. The achievement of concentration balance for electrolytes is accelerated by setting $J_{UF}$=$J_{Ref}$=0.8 L/h in this phase, and thus blood volume is kept constant. For notation purposes, t=0 indicates the start of the 3-h experimental phase. Eight sessions were carried out with UF, refilling and sodium steps. Two sessions were carried out with $J_{UF}$=$J_{Ref}$=0 to evaluate the isolated effects of $Na_{Pl}$ variations on the measurement system. Two sessions were carried out with constant Nam concentration to evaluate the isolated effect of ΔRBV. Of the last two sessions, one was carried out with $Na_{Pl}(0)$=$Na_{Ref}$=140 mM, whereas the other with $Na_{Pl}(0)$=$Na_{Ref}$=145 mM to simulate a realistic case with a hyper-natremic patient.

Samples for blood gas analysis were taken at the start and end of the session and at each 45 min in-between (indicated as black dots in FIG. 5). A Stat Profile pHOx Ultra blood gas analyzer (Nova Biomedical, Waltham MA, USA) was used to determine electrolyte concentration. At the end of each session, the internal session log of the hemodialysis machine was downloaded to access internal sensor data (ultrafiltration rate $J_{UF}$, dialysate inlet conductivity $\sigma_{In}$, dialysate outlet conductivity $\sigma_{Out}$), see FIG. 6.

Data recorded from the optical measurement system were subjected to median filtering for artefact removal (10-sample window) followed by moving average smoothing (5000-sample window). Data from the 3-h experimental phase was then converted to relative optical power variations according to:

$$\Delta RP_i(t) = \frac{V_{Out,i}(t) - V_{Out,i}(0)}{V_{Out,i}(0)} \quad i = 1, 2, 3, 4 \quad (5)$$

where $V_{Out,i}(t)$ is the recorded analog voltage output and i indicates output channel.

The signals $J_{UF}(t)$, $\sigma_{In}(t)$ and $\sigma_{Out}(t)$ were recorded by the session logger of the extracorporeal blood treatment machine at $F_S$=0.1 Hz. As for the optical data, only data from the 3-h experimental phase was analysed. The signal $J_{UF}(t)$ underwent median filtering (5-sample window) for artefact removal, whereas $\sigma_{In}(t)$ and gout(t) were smoothed by moving average filtering (5-sample window).

Throughout the session, the hemodialysis machine is temporarily switched to bypass mode, either for safety reasons or for the purpose of internal recalibration. During bypass, ultrafiltration is suspended and the hydraulic connection of dialysate to the hemodialyzer is short-circuited, see FIG. 6 (dotted line), meaning that data from the conductivity cells ($\sigma_{In}(t)$, $\sigma_{Out}(t)$) is not useful during by-pass condition since the inlet fresh dialysis fluid is directly routed towards the effluent line without entering the filtration unit. Using the session log, a binary signal indicating whether conductivity data is available at any given time was built for each session.

Blood gas analysis was used to determine the experimental plasmatic sodium concentration $Na_{Pl,Exp}(t)$ at t=0, 45, 90, 135 and 180 min. Three analyses were carried out on each sample to get an average value, but the first measurement in each group of three always showed negative bias, whereas the other two were consistent among them. For this reason, the value of $Na_{Pl,Exp}(t)$ was, for each blood sample, computed as the average of the second and third measurements. A possible explanation is that the first measurement is the one that is carried out after a period of inactivity of the analyser and operating conditions of the instrument might be slightly different.

Results of Experimental Session

As described, the parameters $G_{Opt}$ in equation (9) and $G_{Na,Gain}$ and $G_{Na,Offset}$ in equation (12) are not based on modeling assumptions, but fitted to experimental data. For this reason, the performance of the system was evaluated in two ways. To determine best performance, the estimation error was computed using a version of the Kalman filter with empirical parameters fitted to the whole dataset. Additionally, to assess the robustness of the estimator, a leave-one-out procedure was employed on the 12-sessions dataset: for each iteration, 11 sessions were employed for fitting and 1 for testing.

The estimation error was calculated for both ΔRBV and $Na_{Pl}$ as the absolute difference between the reference data and the estimates. The mean and maximum errors were first computed for each session; then the inter-session mean±standard deviation was calculated for both quantities. The results are reported in below Table I.

TABLE I

RESULTS OF THE ESTIMATION PROCESS

| ESTIMATION CONDITIONS | ERROR | MEAN ± SD | MAX ± SD |
|---|---|---|---|
| Complete Dataset | ΔRBV [%] | 0.97 ± 0.73 | 1.90 ± 0.95 |
|  | $Na_{Pl}$ [mM] | 0.47 ± 0.19 | 2.35 ± 1.38 |
| Leave-One-Out | ΔRBV [%] | 0.99 ± 0.65 | 2.10 ± 0.97 |
|  | $Na_{Pl}$ [mM] | 0.51 ± 0.15 | 2.54 ± 1.33 |

The Kalman filter, tuned with data from the whole dataset, showed good performance when estimating ΔRBV and $Na_{Pl}$.

The estimation errors evaluated with the leave-one-out procedure present only small differences compared to evaluation on the whole dataset, especially if the large standard deviations are taken into account. This result indicates that the fitting procedure is not sensitive to data from one session in particular, and demonstrates the reliability of the proposed filter architecture.

Figure 10:
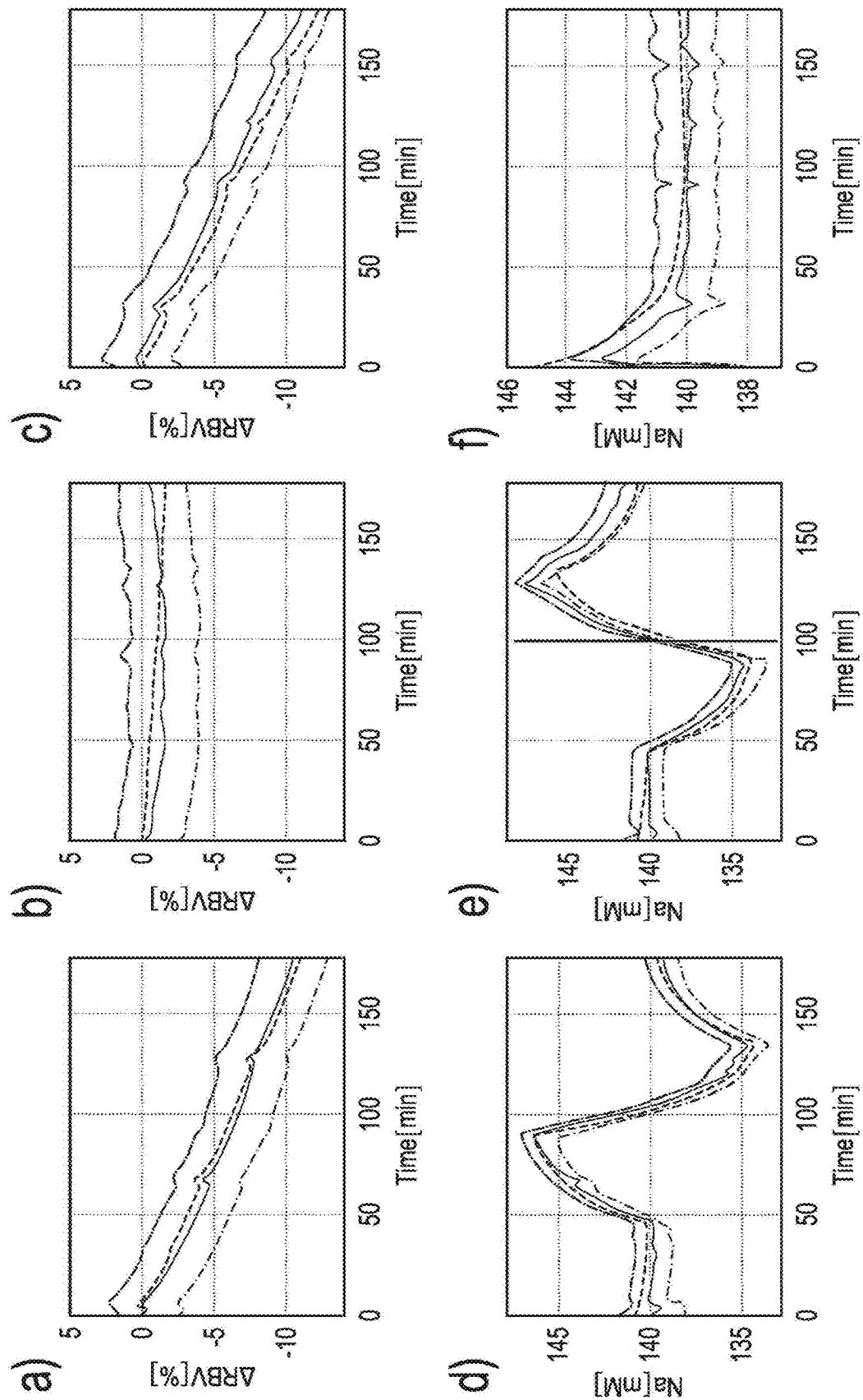

FIG. 10 exemplifies state estimation results in the best case, when parameters of the estimator are computed using data from the complete dataset. The estimates of ΔRBV and $Na_{Pl}$ are presented for an experiment with both blood volume loss and sodium concentration steps (FIGS. 10(a) and 10(d) respectively), for an experiment with blood volume loss close to zero (FIGS. 10(b) and 10(e)) and for an experiment in which a starting hypernatremic patient condition is simulated (FIGS. 10(c) and 10(f)). The switch from standard filter operation to bypass mode is represented by the temporary transition to dark grey solid lines. FIGS. 10(a)-(c) show results on the estimation of relative blood volume loss. Although some difference remains between estimated and reference blood volume loss, the trend of $Na_{Pl}$ does not show any recognizable influence on the ΔRBV signal. This feature is observable in all experimental sessions and indicates that the target of an osmolarity-insensitive ΔRBV estimation is reached. FIG. 10(f) is an example of the reliable behaviour of the estimator, even when the starting conditions are less-than-optimal: the starting plasmatic sodium concentration of the simulated patient is much higher than the starting estimate of the Kalman filter (145 vs 140 mM). Nonetheless, the estimator can drive the estimate of $Na_{Pl}$ in the direction of the experimental value. After less than 10 min from session onset, the estimated confidence interval, given by $Na_{Pl}±\sqrt{P_{22}}$, already includes reference data. Such a short time period is largely compatible with clinical usefulness for $Na_{Pl}$ estimation.

The $P^+$ matrix, being updated at each step, is bound to converge to a steady-state value due to the properties of the Kalman filter algorithm. It is clear from the dynamics of boundary intervals of the estimates shown in FIG. 10 that $P^+$ reaches steady-state very quickly, in the first few minutes of filter operation (≅2 min).

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. A non-invasive blood volume sensor for determining at least one property of blood flowing in an extracorporeal segment of an extracorporeal blood treatment apparatus comprising:
   at least one source for directing a signal towards the blood along an emission axis;
   a plurality of detectors configured to receive the signal emitted by the at least one source after the signal at least partially passes through the blood flowing in the extracorporeal segment, and to emit respective output signals related to the received signal; and
   a controller configured to receive the respective output signals from the plurality of detectors and to determine a value of the at least one property of the blood based on the output signals, wherein the property of the blood is one of a blood volume variation, a hemoglobin concentration change, or a parameter related to the blood volume variation or the hemoglobin concentration;
   wherein the controller is further configured to use a state-space mathematical model for determining the value of the at least one property of the blood and/or an auxiliary blood parameter, wherein the state-space mathematical model includes the following equations:

$$\Delta \dot{R}BV(t) = 0$$

$$\dot{Na}_{Pl}(t) = \frac{Na_{In}(t) - Na_{Pl}(t)}{\tau_{Diff}}$$

wherein
   $\Delta \dot{R}BV(t)$ is a differential relative blood volume,
   $\dot{Na}_{pl}(t)$ is a differential plasma sodium concentration in the extracorporeal segment at instant t,
   $Na_{pl}(t)$ is a plasma sodium concentration in the extracorporeal segment at instant t,
   $Na_{In}(t)$ is an inlet dialysate sodium concentration at instant t at an inlet of a filtration unit, and
   $\tau_{Diff}$ is a diffusion time; wherein the diffusion time is approximate to a constant time, included between 1000 and 1200 seconds.

2. The non-invasive blood volume sensor according to claim 1, wherein the controller is further configured to determine a value and a time variation of the auxiliary blood parameter based on the output signals from the plurality of detectors, the auxiliary parameter being chosen from the group consisting of: plasma conductivity, a plasma conductivity-related parameter, a concentration of at least one substance in the blood, and a concentration-related parameter of at least one substance in the blood.

3. The non-invasive blood volume sensor according to claim 1, wherein the controller is further configured to:
receive values for a sodium concentration of an inlet dialysis fluid flowing in a preparation line of the extracorporeal blood treatment apparatus, and
determine the value of the at least one property of the blood and the auxiliary blood parameter based on the inlet dialysis fluid sodium concentration.

4. The non-invasive blood volume sensor according to claim 1, wherein the controller is further configured to:
receive values for a conductivity of an inlet dialysis fluid flowing in a preparation line of the extracorporeal blood treatment apparatus, and
determine the value of the at least one property of the blood and the auxiliary blood parameter based on the inlet dialysis fluid conductivity.

5. The non-invasive blood volume sensor according to claim 1, wherein the controller is further configured to:
receive values for a conductivity of an outlet dialysis fluid flowing in a spent dialysate line of the extracorporeal blood treatment apparatus, and
determine the value of the at least one property of the blood and the auxiliary blood parameter based on the outlet dialysis fluid conductivity.

6. The non-invasive blood volume sensor according to claim 1, wherein the diffusion time is equal to:

$$\tau_{Diff} = \frac{V_B(t)}{K_{Diff}}$$

wherein
$V_B(t)$ is an absolute blood volume at instant t, and
$K_{Diff}$ is a semipermeable membrane diffusion coefficient for sodium.

7. The non-invasive blood volume sensor according to claim 1, wherein the controller is further configured to determine both the value of the at least one property of the blood and an auxiliary blood parameter based on the output signals from the plurality of detectors using a mathematical equation linearly combining values of the at least one property of the blood, of the auxiliary blood parameter and of the output signals.

8. The non-invasive blood volume sensor according to claim 1, wherein the controller is further configured to determine both the value of the at least one property of the blood and an auxiliary blood parameter based on the output signals from the plurality of detectors using the following mathematical equation:

$$\Delta RP_i(t) = G_{opt,i,1} \cdot \Delta RBV(t) + G_{opt,i,2} \cdot Na_{pl}(t) + G_{opt,i,3}$$

wherein
$\Delta RP_i(t)$ is an optical output of detector i,
$G_{opt,i,1}$ is a first coefficient for the output signal from detector i,
$G_{opt,i,2}$ s a second coefficient for the output signal from detector i,
$G_{opt,i,3}$ is a third coefficient for the output signal from detector i,
$\Delta RBV(t)$ is a relative blood volume, and
$Na_{Pl}(t)$ is a plasma sodium concentration in the extracorporeal segment at instant t.

9. The non-invasive blood volume sensor according to claim 1, wherein the controller is further configured to use a state-space mathematical model for determining the value of the at least one property of the blood and/or an auxiliary blood parameter, wherein in a by-pass condition of the extracorporeal blood treatment apparatus the inlet dialysis fluid is not routed into, and by-passes, a filtration unit, the state-space mathematical model includes the following equations:

$$\Delta R\dot{B}V(t) = 0$$

$$Na\dot{}_{Pl}(t) = 0$$

wherein
$\Delta RBV(t)$ is a differential relative blood volume, and
$Na_{Pl}(t)$ is a differential plasma sodium concentration in the extracorporeal segment at instant t.

10. The non-invasive blood volume sensor according to claim 1, wherein the controller is further configured to determine an auxiliary blood parameter based on an outlet dialysis fluid conductivity modeled as an average of an inlet dialysis fluid conductivity and of a plasma conductivity, wherein the outlet dialysis fluid conductivity is the conductivity of a dialysis fluid flowing in a spent dialysate line of the extracorporeal blood treatment apparatus, the inlet dialysis fluid conductivity is the conductivity of a dialysis fluid flowing in a preparation line of the extracorporeal blood treatment apparatus, and the plasma conductivity is the conductivity of the blood flowing in the extracorporeal segment.

11. The non-invasive blood volume sensor according to claim 1, wherein the controller is further configured to determine an auxiliary blood parameter based on the following equation:

$$\sigma_{Out}(t) = G_{Mix} \cdot \sigma_{Pl}(t) + (1 - G_{Mix}) \cdot \sigma_{in}(t - \tau_{Delay})$$

wherein
$\sigma_{in}(t)$ is an inlet dialysate conductivity at instant t at the inlet of the filtration unit,
$\sigma_{out}(t)$ is an outlet dialysate conductivity at instant t at the outlet of the filtration unit,
$\sigma_{pl}(t)$ is a plasmatic conductivity in the extracorporeal segment at instant t,
$G_{Mix}$ is a weighing coefficient, and
$\tau_{Delay}$ is a delay time to account for the propagation time of changes in the inlet dialysate composition across the hydraulic circuit.

12. The non-invasive blood volume sensor according to claim 11, wherein the weighing coefficient is proportional or equal to:

$$G_{Mix} = \frac{D}{J_D}$$

wherein
D is a treatment unit dialysance, and
$J_D$ is a dialysis flow rate, and
wherein the weighing coefficient is a constant value between 0.4 and 0.6.

13. The non-invasive blood volume sensor according to claim 11, wherein the delay time to account for the propagation time of changes in the inlet dialysate composition across the hydraulic circuit is a constant value.

14. The non-invasive blood volume sensor according to claim 1, wherein the controller is further configured to determine an auxiliary blood parameter based on a plasma conductivity, which is the conductivity of the blood flowing in the extracorporeal segment.

15. The non-invasive blood volume sensor according to claim 1, wherein the controller is further configured to determine an auxiliary blood parameter based on the following equation:

$$\sigma_{Pl}(t) = G_{Na,Gain} \cdot Na_{pl}(t) + G_{Na,Offset}$$

wherein
$\sigma_{pl}(t)$ is a plasmatic conductivity in the extracorporeal segment at instant t,
$G_{Na,Gain}$ is a constant coefficient,
$G_{Na,Offset}$ is a constant coefficient, and
$Na_{pl}(t)$ is a plasma sodium concentration in the extracorporeal segment at instant t.

16. The non-invasive blood volume sensor according to claim 1, wherein the controller is further configured to use a Kalman filter for determining the value of the at least one property of the blood and/or an auxiliary blood parameter.

17. The non-invasive blood volume sensor according to claim 1, wherein at least one detector includes a photodiode receiver.

18. The non-invasive blood volume sensor according to claim 1, wherein the at least one source includes a light emitter or an ultrasound emitter, and
wherein the at least one source includes a fiber optic having one end coupled with a signal emitter of the at least one source and the other end placed to direct the emitted signal towards the blood along the emission axis.

19. The non-invasive blood volume sensor according to claim 18, wherein the signal emitter is a multiple wavelength LED emitter that includes multiple LEDs on a same chip with pick wavelengths in the red and infrared bands, and wherein an illuminating peak wavelength of the at least one source is between 790 nm and 820 nm.

20. The non-invasive blood volume sensor according to claim 1, wherein the plurality of detectors are placed at different angular degrees with respect to the emission axis to collect reflected signal, scattered signal and transmitted signal depending on their respective positions, wherein a first detector is placed at about 180° with respect to the emission axis of the source, and/or a second detector is placed at about 90° with respect to the emission axis of the source, and/or a third detector is placed at about 45° with respect to the emission axis of the source, and/or a fourth detector being is placed at about 0° with respect to the emission axis of the source, and
wherein the plurality of detectors are configured to receive the signal emitted by the at least one source radially along a normal section of the blood flow in a tube or segment of the extracorporeal blood treatment apparatus.

21. The non-invasive blood volume sensor according to claim 1, wherein each of the plurality of detectors receives direct, reflected or refracted signal along a respective receiving axis, the respective receiving axes of each of the plurality of detectors and the emission axis of the at least one source being contained in a same plane.

22. The non-invasive blood volume sensor according to claim 1, wherein the extracorporeal segment of the extracorporeal blood treatment apparatus is a tube portion, the tube portion having a substantially circular cross section, wherein the plurality of detectors and the at least one source are disposed around the tube portion at different angular degrees and around the same cross sectional plane of the tube portion, and wherein the plurality of detectors are configured to receive the signal emitted by the at least one source radially along a normal section of the blood flow in the tube portion.

23. The non-invasive blood volume sensor according to claim 1, wherein the extracorporeal segment of the extracorporeal blood treatment apparatus is a tube portion, the non-invasive blood volume sensor further comprising a housing having one portion which is counter-shaped to the tube portion, the housing being made of two or more pieces defining a through passage counter-shaped to the outer shape of the tube portion to house the tube portion inside the through passage, wherein each of the plurality of detectors includes a respective end placed at the counter-shaped portion facing the tube portion in a coupling condition of the hosing with the tube portion, and wherein a signal emitter of the at least one source includes an end placed at the counter-shaped portion facing the tube portion in a coupling condition of the hosing with the tube portion.

24. The non-invasive blood volume sensor according to claim 23, wherein the at least one source includes a first fiber optic having one end coupled with the signal emitter and the other end fixed to the housing, the other end of the first fiber optic being placed at the counter-shaped portion and facing the tube portion in a coupling condition of the housing with the tube portion,
wherein at least a first detector includes a second fiber optic, one end of the second fiber optic in correspondence with the tube portion is fixed to the housing, the other end of the second fiber optic being placed at the counter-shaped portion and facing the tube portion in a coupling condition of the housing with the tube portion, wherein at least a second detector includes a third fiber optic, one end of the third fiber optic being placed in correspondence with the tube portion, the other end of the third fiber optic being coupled to a receiver.

25. The non-invasive blood volume sensor according to claim 24, wherein the end of the third fiber optic in correspondence with the tube portion is fixed to a housing having one portion which is counter-shaped to the tube portion of the extracorporeal blood treatment apparatus, the end of the third fiber optic being placed at the counter-shaped portion and facing the tube portion in a coupling condition of the housing with the tube portion.

26. The non-invasive blood volume sensor according to claim 25, including a printed circuit board including circuitry for transimpedance amplification, wherein each of the plurality of detectors includes respective photodiode receivers connected to the printed circuit board, wherein the circuitry for transimpedance amplification is a current-to-voltage converter and amplifies a current output of the plurality of detectors, and wherein the printed circuit board includes lowpass filtering for filtering the signals exiting the circuitry for transimpedance amplification.

27. A non-invasive blood volume sensor for determining at least one property of blood flowing in an extracorporeal tube portion of an extracorporeal blood treatment apparatus comprising:
a housing having one portion which is counter-shaped to the extracorporeal tube portion and made of two or more pieces defining a through passage counter-shaped to the outer shape of the extracorporeal tube portion to house the tube portion inside the through passage;

at least one source for directing a signal towards the blood along an emission axis, wherein the at least one source includes a first fiber optic having one end coupled with a signal emitter and the other end fixed to the housing, the other end of the first fiber optic being placed at the counter-shaped portion and facing the extracorporeal tube portion in a coupling condition of the housing with the extracorporeal tube portion;

a plurality of detectors configured to receive the signal emitted by the at least one source after the signal at least partially passes through the blood flowing in the extracorporeal tube portion, and to emit respective output signals related to the received signal, wherein each of the plurality of detectors includes a respective end placed at the counter-shaped portion facing the tube portion in a coupling condition of the housing with the tube portion, wherein a first detector includes a second fiber optic, one end of the second fiber optic in correspondence with the extracorporeal tube portion is fixed to the housing, the other end of the second fiber optic being placed at the counter-shaped portion and facing the extracorporeal tube portion in a coupling condition of the housing with the extracorporeal tube portion, wherein a second detector includes a third fiber optic, one end of the third fiber optic being fixed to the housing, being placed at the counter-shaped portion and facing the extracorporeal tube portion in a coupling condition of the housing with the extracorporeal tube portion, the other end of the third fiber optic being coupled to a receiver;

a printed circuit board including circuitry for transimpedance amplification, wherein each of the plurality of detectors includes respective photodiode receivers connected to the printed circuit board, wherein the circuitry for transimpedance amplification is a current-to-voltage converter and amplifies a current output of the plurality of detectors, and wherein the printed circuit board includes lowpass filtering for filtering the signals exiting the circuitry for transimpedance amplification; and a controller configured to receive the respective output signals from the plurality of detectors and to determine a value of the at least one property of the blood based on the output signals, wherein the property of the blood is one of a blood volume variation, a hemoglobin concentration change, or a parameter related to the blood volume variation or the hemoglobin concentration.

28. The non-invasive blood volume sensor according to claim 27, wherein the controller is further configured to use a state-space mathematical model for determining the value of the at least one property of the blood and/or the auxiliary blood parameter, wherein the state-space mathematical model includes the following equations:

$$\Delta R\dot{B}V(t) = 0$$

$$Na'_{Pl}(t) = \frac{Na_{In}(t) - Na_{Pl}(t)}{\tau_{Diff}}$$

wherein
$\Delta R\dot{}BV(t)$ is a differential relative blood volume,
$N\dot{a}_{Pl}(t)$ is a differential plasma sodium concentration in the extracorporeal segment at instant t,
$Na_{Pl}(t)$ is a plasma sodium concentration in the extracorporeal segment at instant t,
$Na_{in}(t)$ is an inlet dialysate sodium concentration at instant t at the inlet of the filtration unit, and
$\tau_{Diff}$ is a diffusion time.

29. The non-invasive blood volume sensor according to claim 27, wherein the diffusion time is approximate to a constant time, included between 1000 and 1200 seconds.

30. A non-invasive blood volume sensor for determining at least one property of blood flowing in an extracorporeal segment of an extracorporeal blood treatment apparatus comprising:

at least one source for directing a signal towards the blood along an emission axis;

a plurality of detectors configured to receive the signal emitted by the at least one source after the signal at least partially passes through the blood flowing in the extracorporeal segment, and to emit respective output signals related to the received signal; and a controller configured to receive the respective output signals from the plurality of detectors and to determine a value of the at least one property of the blood based on the output signals, wherein the property of the blood is one of a blood volume variation, a hemoglobin concentration change, or a parameter related to the blood volume variation or the hemoglobin concentration, wherein the controller is further configured to use a state-space mathematical model for determining the value of the at least one property of the blood and/or an auxiliary blood parameter, wherein the state-space mathematical model includes the following equations:

$$\Delta R\dot{B}V(t) = 0$$

$$Na'_{Pl}(t) = \frac{Na_{In}(t) - Na_{Pl}(t)}{\tau_{Diff}}$$

wherein
$\Delta R\dot{}BV(t)$ is a differential relative blood volume,
$N\dot{a}_{Pl}(t)$ is a differential plasma sodium concentration in the extracorporeal segment at instant t,
$Na_{Pl}(t)$ is a plasma sodium concentration in the extracorporeal segment at instant t,
$Na_{in}(t)$ is an inlet dialysate sodium concentration at instant t at an inlet of a filtration unit, and
$\tau_{Diff}$ is a diffusion time; wherein the diffusion time is equal to:

$$\tau_{Diff} = \frac{V_B(t)}{K_{Diff}}$$

wherein
$V_B(t)$ is an absolute blood volume at instant t, and
$K_{Diff}$ is a semipermeable membrane diffusion coefficient for sodium.

* * * * *